(12) United States Patent
Chen et al.

(10) Patent No.: US 7,514,435 B2
(45) Date of Patent: Apr. 7, 2009

(54) PYRROLOTRIAZINE KINASE INHIBITORS

(75) Inventors: Ping Chen, Belle Mead, NJ (US); Yufen Zhao, Pennington, NJ (US); Brian E. Fink, Yardley, PA (US); Soong-Hoon Kim, Titusville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/560,378

(22) Filed: Nov. 16, 2006

(65) Prior Publication Data

US 2007/0149534 A1 Jun. 28, 2007

Related U.S. Application Data

(60) Provisional application No. 60/738,269, filed on Nov. 18, 2005.

(51) Int. Cl.
C07D 487/04 (2006.01)
C07D 401/06 (2006.01)
A61K 31/4412 (2006.01)
A61K 31/4427 (2006.01)
A61K 31/53 (2006.01)
A61P 19/02 (2006.01)
A61P 35/00 (2006.01)

(52) U.S. Cl. .................................. 514/243; 544/183
(58) Field of Classification Search ............. 544/183; 514/243
See application file for complete search history.

(56) References Cited

U.S. PATENT DOCUMENTS

| | | | |
|---|---|---|---|
| 6,670,357 B2 | 12/2003 | Leftheris et al. |
| 6,787,545 B1 | 9/2004 | Ohtani et al. |
| 6,867,300 B2 | 3/2005 | Godfrey, Jr. et al. |
| 6,869,952 B2 | 3/2005 | Bhide et al. |
| 6,908,916 B2 | 6/2005 | Mastalerz et al. |
| 6,916,815 B2 | 7/2005 | Vite et al. |
| 6,933,386 B2 | 8/2005 | Bhide et al. |
| 6,951,859 B2 | 10/2005 | Bhide et al. |
| 6,969,717 B2 | 11/2005 | Bhide et al. |
| 7,030,118 B2 | 4/2006 | Lombardo et al. |
| 7,064,203 B2 | 6/2006 | Gavai et al. |
| 7,102,001 B2 | 9/2006 | Swaminathan et al. |
| 7,102,002 B2 | 9/2006 | Cai et al. |
| 7,102,003 B2 | 9/2006 | Gavai et al. |
| 7,151,176 B2 | 12/2006 | Gavai et al. |
| 2003/0232831 A1 | 12/2003 | Dyckman et al. |
| 2004/0229877 A1 | 11/2004 | Leftheris et al. |

FOREIGN PATENT DOCUMENTS

| | | |
|---|---|---|
| WO | WO 98/08847 | 3/1998 |
| WO | WO 00/71129 | 11/2000 |
| WO | WO-2000/71129 A1 * | 11/2000 |
| WO | WO 02/40486 | 5/2002 |
| WO | WO 03/027111 | 4/2003 |
| WO | WO 2005/049033 | 6/2005 |
| WO | WO-2005/121147 A1 * | 12/2005 |

OTHER PUBLICATIONS

Cecil Textbook of Medicine, edited by Bennet, J.C., and Plum F., 20th edition, vol. 1, 1004-1010, 1996.*
Mass, R. D., Int. J. Radiation Oncology Bio. Phys. vol. 58(3): 932-940, 2004.*
Fabbro et al. Pharmacology & therapeutics 93, 79-98, 2002.*
Patil, S.A. et al., "Synthesis of Pyrrolo[2,1-*f*][1,2,4]triazine Congeners of Nucleic Acid Purines via the *N*-Amination of 2-Substituted Pyrroles", J. Heterocyclic Chem., vol. 31, pp. 781-786 (1994).
Quintela, J.M. et al., "A Ready One-pot Preparation for Pyrrolo[2,1-*f*][1,2,4]triazine and Pyrazolo[5,1-*c*]pyrimido[4,5-*e*]-[1,2,4]triazine Derivatives", Tetrahedron, vol. 52, No. 8, pp. 3037-3048 (1996).
Hunt, J.T. et al., "Discovery of the Pyrrolo[2,1-f][1,2,4]triazine Nucleus as a New Kinase Inhibitor Template", J. Med. Chem., vol. 47, No. 16, pp. 4054-4059 (2004).
Migliara, O. et al., "Synthesis of a New Bridgehead Nitrogen Heterocyclic System. Pyrrolo[2,1-*f*]-1,2,4-triazine Derivatives", J. Heterocyclic Chem., vol. 16, pp. 833-834 (1979).

* cited by examiner

Primary Examiner—Venkataraman Balasubramanian
(74) Attorney, Agent, or Firm—Elliott Korsen

(57) ABSTRACT

The present invention provides compounds of formula I

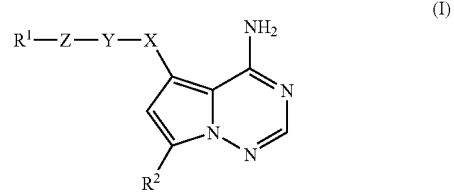

and pharmaceutically acceptable salts thereof.

The formula I compounds inhibit tyrosine kinase activity of Trk receptors such as TrkA, TrkB, TrkC or Flt-3 thereby making them useful as antiproliferative agents.

6 Claims, No Drawings

PYRROLOTRIAZINE KINASE INHIBITORS

This application claims priority benefit under Title 35 § 119(e) of U.S. Provisional Application No. 60/738,269, filed on Nov. 18, 2005, incorporated herein by reference in its entirety.

FIELD OF THE INVENTION

This invention relates to novel pyrrolotriazine compounds that are useful as anti-cancer agents. This invention also relates to a method of using the compounds in the treatment of proliferative diseases and to pharmaceutical compositions containing the compounds.

BACKGROUND OF THE INVENTION

Tropomysosin Related Kinases (Trk) are a family of receptor tyrosine kinases composed of three family members, TrkA, TrkB and TrkC. The Trks bind with high affinity to, and mediate the signal transduction induced by the Neurotrophin family of ligands whose prototype members are Nerve Growth Factor (NGF), Brain-Derived Neurotrophic Factor (BDNF) and Neurotrophin-3, -4 and -5 (NT-3, NT-4 and NT-5). In addition, a co-receptor lacking enzymatic activity, p75, has been identified which binds all neurotrophines (NTs) with low affinity and regulates neurotrophin signaling. A critical role of the Trks and their ligands during the development of the central and peripheral nervous systems have been established through gene disruption studies in mice. In particular, TrkA-NGF interaction was shown as a requirement for the survival of certain peripheral neuron populations involved in mediating pain signaling. In addition to these developmental consequences of Trk signaling, the subversion of this receptor and its signaling pathway in certain malignancies has also been documented. Of particular note are reports of aberrant expression of NGF and TrkA receptor kinase are implicated in the development and progression of human prostatic carcinoma and pancreatic ductal adrenocarcinoma and activating chromosomal rearrangements of Trks in acute myelogenous leukemia (AML), thyroid and breast cancers and receptor point mutations predicted to be constitutively activating in colon tumors. In addition to these activation mechanisms, elevated Trk receptor and ligand have also been reported in a variety of tumor types including multiple myeloma, melanoma, neuroblastoma, ovarian and pancreatic carcinoma. The neurotrophins and their corresponding Trk receptor subtypes have been shown to exert a variety of pleiotropic responses on malignant cells, including enhanced tumor invasiveness and chemotaxis, activation of apoptosis, stimulation of clonal growth, and altered cell morphology. These effects have been observed in carcinomas of the prostate, breast, thyroid, colon, malignant melanomas, lung carcinomas, glioblastomas, pancreatic carcinoids and a wide variety of pediatric and neuroectodermal-derived tumors including Wilm's tumor, neuroblastomas and medulloblastomas. Neurotrophins and their receptor subtypes have been implicated in these cancers either through autocrine or paracrine mechanisms involving carcinoma cells and the surrounding parenchymal and stromal tissues. In addition, profound or significantly attenuated reduction of bone pain caused by prostate cancer metastasis has recently been achieved by utilization of anti-NGF antibody. Overall, the oncogenic properties of Trk signaling in multiple tumor types makes the modulation of the Trk receptor signaling a potentially attractive therapeutic intervention point in different malignancies.

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. In general, RTKs are activated by ligand-induced oligomerization and tyrosine autophosphorylation of specific intracellular substrates such as PLCγ, PI3 kinase, ras, and raf./MEK/Erk1. Tyrosine kinase activity is an absolute requirement for signal transduction through this class of receptor.

The Trk family of RTKs is frequently expressed in lung, breast, pancreatic and prostate cancers as well as in certain type of acute myelogenous leukemia and congenital fibrosarcoma. The tyrosine kinase activity of Trk is believed to promote the unregulated activation of cell proliferation machinery. It is believed that inhibitors of either TrkA, TrkB, or TrkC kinases, individually or in combination, have utility against some of the most common cancers such as brain, melanoma, multiple myeloma, squamous cell, bladder, gastric, pancreatic, breast, head, neck, esophageal, prostate, colorectal, lung, renal, ovarian, gynecological, thyroid cancer, and certain type of hematological malignancies.

DETAILED DESCRIPTION OF THE INVENTION

The invention provides for compounds of formula I, pharmaceutical compositions employing such compounds and for methods of using such compounds.

In accordance with the present invention, there are disclosed compounds of formula I

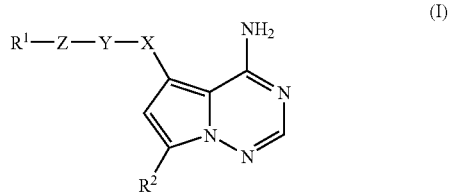

wherein the symbols have the following meanings and are, for each occurrence, independently selected:

X is a direct bond, —C=O— or —CH—OH;

Y is $C_3$-$C_8$ cycloalkyl, $C_6$-$C_{10}$ aryl, a 5 to 13 membered heteroaromatic ring, $C_3$-$C_8$ alkyl or a 4 to 8 membered heteroalkyl ring, each of said Y groups optionally substituted with 1 to 3 groups selected from the group consisting of halogen, —OH, alkyl, substituted alkyl, —CN, —NH$_2$, —CONHR$^3$, —OCONHR$^3$, —CONHSO$_2$R$^3$, —NHCONHR$^3$, —CH$_2$OR$^3$, —CH$_2$CH$_2$OH, alkoxy, substituted alkoxy, aryl, substituted aryl, aryloxy, substituted aryloxy, —CF$_3$ and —OCF$_3$, two of which may be attached to the same ring carbon atom provided that the resultant compound is chemically stable;

Z is —(CH$_2$)$_p$— where p is an integer from 0 to 5, —O—, —S—, —S(O)—, —S(O)$_2$—, —S(O)$_2$NR$^4$—, —NR$_4$—, —NR$^4$SO$_2$—, —NR$^4$C(=O)—, —NR$^4$C(=O)NR$^5$—, —NR$^4$C(=NH)NR$^5$—, —NR$^4$C(=N—CN)NR$^5$—, —NR$^4$C(=N—OR$^6$)NR$^5$—, —NR$^4$S(=O)NR$^5$—, —NR$^4$SO$_2$NR$^5$—, —NR$^4$SO$_2$CHR$^5$—, —CHR$^4$SO$_2$NR$^5$—, —NR$^4$SO$_2$—, —NR$^4$C(=O)O—, —OC(=O)NR—, —CHR$^4$C(=O)NR$^5$—, —NR$^4$C(=O)CHR$^5$—, —CHR$^4$NR$^5$C(=O)—, —C(=O)

NR$^4$CHR$^5$—, —CHR$^4$NSO$_2$—, —CHR$^4$C(=N—OR)—, —CHR$^4$C(=N—OR$^6$)NR$^5$—, —CHR$^4$SO$_2$NR$^5$—, —C(=O)NR$^4$C(=O)—, —CHR$^4$C(=O)NR$^5$C(=O)—, —NR$^4$C(=O)NR$^5$C(=O)—, wherein each of R$^4$, R$^5$ and R$^6$ groups are independently selected from H, C$_1$-C$_6$ alkyl, C$_3$-C$_6$ cycloalkyl, C$_1$-C$_6$ acyl, C$_6$-aromatic group and 5 or 6-membered heteroaromatic group, wherein each of the foregoing R$^4$, R$^5$ and R$^6$ groups are independently optionally substituted with 1-3 halogen atoms, C$_1$-C$_6$ alkyl, C$_3$-C$_6$ cycloalkyl, and C$_1$-C$_6$ alkoxy;

R$^1$ is H, C$_1$-C$_6$ alkyl, arylalkyl, C$_3$-C$_8$ cycloalkyl, C$_9$-C$_{14}$ bicycloalkyl, C$_6$-C$_{10}$ aryl, C$_5$-C$_{13}$ heteroaryl, C$_4$-C$_{12}$ heterocyclyl and 3 to 8-membered heterocycloalkyl and each of said groups optionally substituted with 1 to 3 groups selected from the group consisting of halogen, —OH, —OR$^7$, —C(=O)OR$^7$—, —S(=O)NHR$^7$, —SO$_2$NHR$^7$, —SO$_2$R$^7$, alkyl, substituted alkyl, —CN, —NHR$^7$, —CONHR$^7$, —OCONHR$^7$, —CONHSO$_2$R$^7$, —NHCONHR$^7$, —CH$_2$OR$^7$, —CH$_2$CH$_2$OH, alkoxy, substituted alkoxy, aryl, substituted aryl, R$^7$ is hydrogen or C$_1$-C$_4$ alkyl; C$_3$-C$_6$ cycloalkyl, aryl, arylalkyl, heteroaryl, heterocyclyl, aryloxy, substituted aryloxy, —CF$_3$ and —OCF$_3$, two of which may be attached to the same ring carbon atom provided that the resultant compound is chemically stable;

R$^2$ is H, halogen, —NR$^8$R$^9$, C$_1$-C$_6$ alkyl, C$_1$-C$_6$ alkenyl, C$_1$-C$_6$ alkynyl, C$_3$-C$_8$ cycloalkyl, arylalkyl or C$_4$-C$_8$ heterocyclyl with at least one atom on the ring selected from nitrogen or oxygen atom, and each of said R$^2$ groups optionally substituted with 1 to 3 groups selected from the group consisting of —OH, OR$^8$, —NH$_2$, —NR$^8$R$^9$, —CONHR$^8$, —OCONHR$^8$, —CONHSO$_2$R$^8$, —NHCONHR$^8$, —SR$^8$, —S(=O)R$^8$, —SO$_2$R$^8$, —SO$_2$NR$^8$R$^9$;

R$^8$ is C$_1$-C$_6$ alkyl, C$_3$-C$_6$ cycloalkyl, an optionally substituted aryl or heteroaryl group; said substituents on the substituted aryl or substituted heteroaryl group are selected from the group consisting of one or more hydrogen, halogen, alkyl, substituted alkyl, alkynyl, substituted alkynyl, alkoxy, substituted alkoxy, aryl, substituted aryl, arylalkyl, substituted arylalkyl, aryloxy and substituted aryloxy;

R$^9$ is hydrogen, halogen, C$_1$-C$_6$ alkyl, C$_3$-C$_6$ cycloalkyl or C$_1$-C$_6$ alkoxy; or R$^8$ and R$^9$ can be taken together with the nitrogen atom to which they are attached to form an optionally substituted heterocyclyl ring;

or a pharmaceutically acceptable salt or stereoisomer thereof.

In another embodiment, the invention comprises a compound of formula II wherein

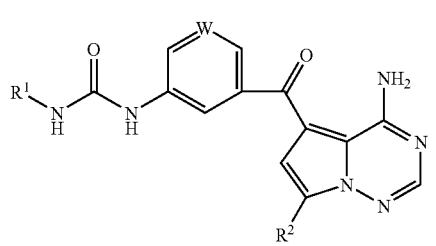

(II)

wherein

W is —CR$^9$— or —N—;

R$^1$ is H, C$_1$-C$_6$ alkyl, arylalkyl, C$_3$-C$_8$ cycloalkyl, C$_9$-C$_{14}$ bicycloalkyl, C$_6$-C$_{10}$ aryl, C$_5$-C$_{13}$ heteroaryl, C$_4$-C$_{12}$ heterocyclyl and 3 to 8-membered heterocycloalkyl and each of said groups optionally substituted with 1 to 3 groups selected from the group consisting of halogen, —OH, —OR$^7$, —C(=O)OR$^7$—, —S(=O)NHR$^7$, —SO$_2$NHR$^7$, —SO$_2$R$^7$, alkyl, substituted alkyl, —CN, —NHR$^7$, —CONHR$^7$, —OCONHR$^7$, —CONHSO$_2$R$^7$, —NHCONHR$^7$, —CH$_2$OR$^7$, —CH$_2$CH$_2$OH, alkoxy, substituted alkoxy, aryl or substituted aryl, R$^7$ is hydrogen or C$_1$-C$_4$ alkyl; C$_3$-C$_6$ cycloalkyl, aryl, arylalkyl, heteroaryl, heterocyclyl, aryloxy, substituted aryloxy, —CF$_3$ and —OCF$_3$, two of which may be attached to the same ring carbon atom provided that the resultant compound is chemically stable;

R$^2$ is H, halogen, —NR$^8$R$^9$, C$_1$-C$_6$ alkyl, C$_1$-C$_6$ alkenyl, C$_1$-C$_6$ alkynyl, C$_3$-C$_8$ cycloalkyl, arylalkyl or C$_4$-C$_8$ heterocyclyl with at least one atom on the ring selected from nitrogen or oxygen atom, and each of said R$^2$ groups optionally substituted with 1 to 3 groups selected from the group consisting of —OH, OR$^8$, —NH$_2$, —NR$^8$R$^9$, —CONHR$^8$, —OCONHR$^8$, —CONHSO$_2$R$^8$, —NHCONHR$^8$, —SR$^8$, —S(=O)R$^8$, —SO$_2$R$^8$, —SO$_2$NR$^8$R$^9$;

R$^8$ is C$_1$-C$_6$ alkyl, C$_3$-C$_6$ cycloalkyl, an optionally substituted aryl or heteroaryl group; said substituents on the substituted aryl or substituted heteroaryl group are selected from the group consisting of one or more hydrogen, halogen, alkyl, substituted alkyl, alkynyl, substituted alkynyl, alkoxy, substituted alkoxy, aryl, substituted aryl, arylalkyl, substituted arylalkyl, aryloxy and substituted aryloxy;

R$^9$ is hydrogen, halogen, C$_1$-C$_6$ alkyl, C$_3$-C$_6$ cycloalkyl or C$_1$-C$_6$ alkoxy; or R$^8$ and R$^9$ can be taken together with the nitrogen atom to which they are attached to form an optionally substituted heterocyclyl ring;

or a pharmaceutically acceptable salt or stereoisomer thereof.

In another embodiment, the invention comprises a compound of formula III

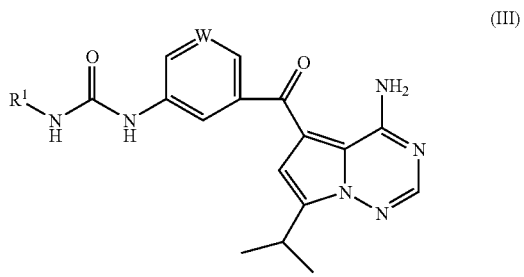

(III)

wherein

W is —CR$^9$— or —N—;

R$^1$ is H, C$_1$-C$_6$ alkyl, arylalkyl, C$_3$-C$_8$ cycloalkyl, C$_9$-C$_{14}$ bicycloalkyl, C$_6$-C$_{10}$ aryl, C$_5$-C$_{13}$ heteroaryl, C$_4$-C$_{12}$ heterocyclyl and 3 to 8-membered heterocycloalkyl and each of said groups optionally substituted with 1 to 3 groups selected from the group consisting of halogen, —OH, —OR$^7$, —C(=O)OR$^7$—, —S(=O)NHR$^7$, —SO$_2$NHR$^7$, —SO$_2$R$^7$, alkyl, substituted alkyl, —CN, —NHR$^7$, —CONHR$^7$, —OCONHR$^7$, —CONHSO$_2$R$^7$, —NHCONHR$^7$, —CH$_2$OR$^7$, —CH$_2$CH$_2$OH, alkoxy, substituted alkoxy, aryl, substituted aryl, R$^7$ is hydrogen or C$_1$-C$_4$ alkyl; C$_3$-C$_6$ cycloalkyl, aryl, arylalkyl, heteroaryl, heterocyclyl, aryloxy, substituted aryloxy, —CF$_3$ and —OCF$_3$, two of which may be attached to the same ring carbon atom provided that the resultant compound is chemically stable;

or a pharmaceutically acceptable salt or stereoisomer thereof.

Preferred compounds of the invention include the following 1-(5-{[4-amino-7-(1-methylethyl)pyrrolo[2,1-f][1,2,4]triazin-5-yl]carbonyl}-3-pyridinyl)-3-(2,4-dichlorophenyl)urea;
1-(3-{[4-amino-7-(1-methylethyl)pyrrolo[2,1-f][1,2,4]triazin-5-yl]carbonyl}phenyl)-3-[3-(1,1-dimethylethyl)-1-methyl-1H-pyrazol-5-yl]urea;
1-(5-{[4-amino-7-(1-methylethyl)pyrrolo[2,1-f][1,2,4]triazin-5-yl]carbonyl}-3-pyridinyl)-3-(2,4-difluorophenyl)urea;
1-(5-{[4-amino-7-(1-methylethyl)pyrrolo[2,1-f][1,2,4]triazin-5-yl]carbonyl}-3-pyridinyl)-3-(2-fluorophenyl)urea;
1-(3-{[4-amino-7-(1-methylethyl)pyrrolo[2,1-f][1,2,4]triazin-5-yl]carbonyl}phenyl)-3-(3-cyclopropyl-1-methyl-1H-pyrazol-5-yl)urea;
1-(5-{[4-amino-7-(1-methylethyl)pyrrolo[2,1-f][1,2,4]triazin-5-yl]carbonyl}-3-pyridinyl)-3-(4-chlorophenyl)urea;
1-(5-{[4-amino-7-(1-methylethyl)pyrrolo[2,1-f][1,2,4]triazin-5-yl]carbonyl}-3-pyridinyl)-3-(2-cyanophenyl)urea;
1-(5-{[4-amino-7-(1-methylethyl)pyrrolo[2,1-f][1,2,4]triazin-5-yl]carbonyl}-3-pyridinyl)-3-[1-methyl-3-(1-methylethyl)-1H-pyrazol-5-yl]urea;
1-[5-({4-amino-7-[3-(dimethylamino)-1-propyn-1-yl]pyrrolo[2,1-f][1,2,4]triazin-5-yl}carbonyl)-3-pyridinyl]-3-(2,4-dichlorophenyl)urea;
1-(5-{[4-amino-7-(1-methylethyl)pyrrolo[2,1-f][1,2,4]triazin-5-yl]carbonyl}-3-pyridinyl)-3-[2-(trifluoromethyl)phenyl]urea;
1-(3-(4-amino-7-(3-(dimethylamino)prop-1-ynyl)pyrrolo[1,2-f][1,2,4]triazine-5-carbonyl)phenyl)-3-(2,4-dichlorophenyl)urea;
1-{3-[(4-amino-7-isopropyl-pyrrolo[2,1-f][1,2,4]triazin-5-yl)carbonyl]phenyl}-3-[4-(trifluoromethyl)phenyl]urea;
1-(3-{[4-amino-7-(1-methylethyl)pyrrolo[2,1-f][1,2,4]triazin-5-yl]carbonyl}phenyl)-3-[3-(1,1-dimethylethyl)-1-(2-hydroxyethyl)-1H-pyrazol-5-yl]urea;
1-{3-[(4-amino-7-isopropyl-pyrrolo[2,1-f][1,2,4]triazin-5-yl)carbonyl]phenyl}-3-(4-bromophenyl)urea;
1-{3-[(4-amino-7-bromopyrrolo[2,1-f][1,2,4]triazin-5-yl)carbonyl]phenyl}-3-(3-cyclopropyl-1-methyl-1H-pyrazol-5-yl)urea;
1-{3-[(4-amino-7-bromopyrrolo[2,1-f][1,2,4]triazin-5-yl)carbonyl]phenyl}-3-(2,4-dichlorophenyl)urea;
1-(3-{[4-amino-7-(1-methylethyl)pyrrolo[2,1-f][1,2,4]triazin-5-yl]carbonyl}phenyl)-3-{3-cyclopropyl-1-[2-(4-morpholinyl)ethyl]-1H-pyrazol-5-yl}urea;
1-(5-{[4-amino-7-(1-methylethyl)pyrrolo[2,1-f][1,2,4]triazin-5-yl]carbonyl}-3-pyridinyl)-3-[4-(dimethylamino)phenyl]urea;
1-[3-({4-amino-7-[3-(dimethylamino)-1-propyn-1-yl]pyrrolo[2,1-f][1,2,4]triazin-5-yl}carbonyl)phenyl]-3-(3-cyclopropyl-1-methyl-1H-pyrazol-5-yl)urea;
1-{3-[(4-amino-7-isopropylpyrrolo[2,1-f][1,2,4]triazin-5-yl)carbonyl]phenyl}-3-(2,4-dichlorophenyl)urea;
1-{3-[(4-amino-7-isopropyl-pyrrolo[2,1-f][1,2,4]triazin-5-yl)carbonyl]phenyl}-3-phenylurea;
1-{3-[(4-amino-7-isopropyl-pyrrolo[2,1-f][1,2,4]triazin-5-yl)carbonyl]phenyl}-3-(2-methoxyphenyl)urea;
1-{3-[(4-amino-7-isopropyl-pyrrolo[2,1-f][1,2,4]triazin-5-yl)carbonyl]phenyl}-3-[2-(trifluoromethyl)phenyl]urea;
1-{3-[(4-amino-7-isopropyl-pyrrolo[2,1-f][1,2,4]triazin-5-yl)carbonyl]phenyl}-3-(3-methoxyphenyl)urea;
1-{3-[(4-amino-7-isopropyl-pyrrolo[2,1-f][1,2,4]triazin-5-yl)carbonyl]phenyl}-3-(3-methylphenyl)urea;
1-{3-[(4-amino-7-isopropyl-pyrrolo[2,1-f][1,2,4]triazin-5-yl)carbonyl]phenyl}-3-(4-fluorophenyl)urea;
1-{3-[(4-amino-7-isopropyl-pyrrolo[2,1-f][1,2,4]triazin-5-yl)carbonyl]phenyl}-3-(4-phenoxyphenyl)urea;
1-{3-[(4-amino-7-isopropyl-pyrrolo[2,1-f][1,2,4]triazin-5-yl)carbonyl]phenyl}-3-(2,4-dimethylphenyl)urea;
1-{3-[(4-amino-7-isopropyl-pyrrolo[2,1-f][1,2,4]triazin-5-yl)carbonyl]phenyl}-3-(1-naphthyl)urea;
1-{3-[(4-amino-7-isopropyl-pyrrolo[2,1-f][1,2,4]triazin-5-yl)carbonyl]phenyl}-3-[4-(dimethylamino)phenyl]urea;
1-{3-[(4-amino-7-isopropyl-pyrrolo[2,1-f][1,2,4]triazin-5-yl)carbonyl]phenyl}-3-[4-(benzyloxy)phenyl]urea;
1-{3-[(4-amino-7-isopropyl-pyrrolo[2,1-f][1,2,4]triazin-5-yl)carbonyl]phenyl}-3-pyridin-3-ylurea;
1-{3-[(4-amino-7-isopropyl-pyrrolo[2,1-f][1,2,4]triazin-5-yl)carbonyl]phenyl}-3-(1,3-benzodioxol-5-yl)urea;
1-{3-[(4-amino-7-isopropyl-pyrrolo[2,1-f][1,2,4]triazin-5-yl)carbonyl]phenyl}-3-(2-naphthyl)urea;
1-{3-[(4-amino-7-isopropyl-pyrrolo[2,1-f][1,2,4]triazin-5-yl)carbonyl]phenyl}-3-biphenyl-2-ylurea;

or a pharmaceutically acceptable salt thereof.

The following are definitions of terms that may be used in the specification. The initial definition provided for a group or term herein applies to that group or term throughout the specification individually or as part of another group, unless otherwise indicated.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. SO$_2$NH$_2$, substituted sulfonamido, nitro, cyano, carboxy, carbamyl, e.g. CONH$_2$, substituted carbamyl e.g. CONHalkyl, CONHaryl, CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. Where noted above where the substituent is further substituted it will be with alkyl, alkoxy, aryl or arylalkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "arylalkyl" refers to an aryl or a substituted aryl group bonded directly through an alkyl group, such as benzyl.

The term "aryloxy" refers to an aryl or a substituted aryl group bonded directly through an alkoxy group, such as methoxy or ethoxy.

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or arylalkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$-$C_7$ carbocylic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclyl" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, homopiperazinyl, 2-oxohomopiperazinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1, 1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl or arylalkyl groups as described above or one or more groups described above as alkyl substituents.

Also included are smaller heterocyclyls, such as, epoxides and aziridines.

The term "carbocyclic ring" or "carbocyclyl" refers to stable, saturated, partially saturated or unsaturated, mono or bicyclic hydrocarbon rings that contain 3-12 atoms. Particularly, this includes a monocyclic ring containing 5 or 6 atoms or a bicyclic ring containing 9 or 10 atoms. Suitable values include cyclopropyl, cyclobutyl, cyclopentyl, cyclohexyl, cycloheptyl, dihydroindenyl and tetrahydronaphthyl. The term "optionally substituted" as it refers to "carbocyclic ring" or "carbocyclyl" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of formula I may also have prodrug forms. Any compound that will be converted in vivo to provide the bioactive agent (i.e., the compound for formula I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzmology*, Vol. 112, p. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, p. 113-191 (1991); and c) H. Bundgaard, *Advanced Drug Delivery Reviews*, 8, 1-38 (1992).

It should further be understood that solvates (e.g., hydrates) of the compounds of formula I are also with the scope of the invention. Methods of solvation are generally known in the art.

Utility

The invention is based on the discovery that certain pyrrolotriazines are inhibitors of protein kinases. More specifically, pyrrolotriazines such as those described in this invention inhibit the protein tyrosine kinase activity of members of the TRK family of receptors. These inhibitors will be useful in the treatment of proliferative diseases that are dependent on signaling by one or more of these receptors. Such diseases include solid tumors of the pancreatic, prostate, lung, head and neck, breast, colon, ovary, as well as other tumor types including multiple myeloma, melanoma, neuroblastoma, gliobalstoma and acute myelogenous leukemia. The invention relates to a pharmaceutical composition of compound of formula I, or pharmaceutically acceptable salt or hydrate thereof, and a pharmaceutically acceptable carrier in the treatment of hyperproliferative disorder in mammal. In particular, said pharmaceutical composition is expected to inhibit the growth and/or metastasis of those primary and recurrent solid tumors which are associated with TrkA, TrkB, TrkC, Flt-3 (Fms-like kinase-3) and Tie-2, especially those tumors which are significantly dependent on TrkA, TrkB, TrkC, Flt-3, Tie-2 for their growth and spread, including for example, cancers of the thyroid, breast, colon, pancreas, or a variety of tumor types including multiple myeloma, melanoma, neuroblastoma and glioblastoma.

Thus according to a further aspect of the invention there is provided the use of a compound of the formula I, or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of formula I or a pharmaceutically acceptable salt thereof as defined herein before.

By virtue of their ability to inhibit TrkA, TrkB, Trk C, Flt-3 and Tie-2 kinases, compounds of the invention can be used for the treatment of proliferative diseases, including cancer. The TrkA, TrkB and TrkC receptor kinases have been shown to be expressed and activated in tumors including thyroid, breast, colon, and elevated Trk receptors and corresponding ligands have also been reported in a variety of tumor types including multiple myeloma, melanoma, pancreatic carcinoma, neuroblastoma and glioblastoma. It is therefore expected that inhibitors of the TrkA, TrkB and TrkC kinases will have efficacy in the treatment of tumors that depend on signaling from either or both of the two receptors. These compounds are expected to have efficacy either as single agent or in combination (simultaneous or sequentially) with other chemotherapeutic agents such as Taxol®, adriamycin, and cisplatin.

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, Zoladex; matrix metalloproteinase inhibitors; VEGF inhibitors, such as anti-VEGF antibodies (Avastin®) and small molecules such as ZD6474 and SU6668; Vatalanib, BAY-43-9006, SU11248, CP-547632, and CEP-7055; HER 1 and HER 2 inhibitors including anti- HER2 antibodies (Herceptin); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, e.g. Gleevec® and Sprycel® (dasatinib); Casodex® (bicalutamide, Astra Zeneca), Tamoxifen; MEK-1 kinase inhibitors, MAPK kinase inhibitors, PI3 kinase inhibitors; PDGF inhibitors, such as imatinib; anti-angiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (ixabepilone), [1S-[1R*,3R*(E),7R*,10S*, 11R*, 12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof; CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g. 6-thioguanine and 6-mercaptopurine; glutamine antagonists, e.g. DON (AT-125; d-oxo-norleucine); ribonucleotide reductase inhibitors; mTOR inhibitors; and haematopoietic growth factors.

Additional cytotoxic agents include, cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein before may be surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, goserelin acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); Intercalating antitumour antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide nitrosoureas, thiotepa; antimitotic agents (for example, vinca alkaloids like vincristine, vinorelbine, vinblastine and vinflunine) and taxoids such as Taxol® (paclitaxel), Taxotere® (docetaxel) and newer microbtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as Velcade® (bortezomib).

As stated above, the formula I compounds of the invention are of interest for their antiproliferative effects. Such compounds of the invention are expected to be useful in a wide range of disease states including cancer, psoriasis, and rheumatoid arthritis.

More specifically, the compounds of formula I are useful in the treatment of a variety of cancers, including (but not limited to) the following:

carcinoma, including that of the prostate, pancreatic ductal adreno-carcinoma, breast, colon, lung, ovary, pancreas, and thyroid;

tumors of the central and peripheral nervous system, including neuroblastoma, glioblastoma, and medulloballstoma and other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease The compounds of formula I are especially useful in treatment of tumors having a high incidence of tyrosine kinase activity, such as prostate, colon, brain, thyroid and pancreatic tumors. By the administration of a composition (or a combination) of the compounds of this invention, development of tumors in a mammalian host is reduced.

Compounds of formula I may also be useful in the treatment of other cancerous diseases (such as acute myelogenous leukemia) that may be associated with signal transduction pathways operating through kinases such as Flt-3 (Fme-like kinase-3, including wild type or any mutant types such as Flt-3(ITD)), Tie-2, CDK2, VEGFR, FGFR and IGFR kinases.

The pharmaceutical compositions of the present invention containing the active ingredient may be in a form suitable for oral use, for example, as tablets, troches, lozenges, aqueous or oily suspensions, dispersible powders or granules, emulsions, hard or soft capsules, or syrups or elixirs.

The pharmaceutical compositions may be in the form of sterile injectable aqueous solutions. Among the acceptable vehicles and solvents that may be employed are water, Ringer's solution and isotonic sodium chloride solution.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

The compounds may be administered in a dosage range of about 0.05 to 200 mg/kg/day, preferably less than 100 mg/kg/day, in a single dose or in 2 to 4 divided doses.

Biological Assays

TrkA

The ability of compounds of the invention to inhibit tyrosine kinase activity of TrkA may be measured using a recombinant enzyme in an assay that measures the ability of compounds to inhibit the phosphorylation of the exogenous substrate, polyGluTyr (PGT, 4:1). The kinase domain of the human TrkA receptor is expressed in Sf9 insect cells as a histidine (His)-fusion protein using a baculovirus expression system. The protein is purified from the lysates of these cells using an Ni-NTA affinity column. After the recombinant enzyme is purified, it is activated by incubation with cold ATP. The enzyme assay is performed in a 96-well plate. Test compounds are first dissolved in dimethylsulfoxide (DMSO) and then serially-diluted in a 96-well plate. The serially-diluted compounds are transferred to the 96-well assay plate so that the final concentration of DMSO in the enzyme assay is 1.64%. All assay components are diluted in phosphorylation buffer (20 mm MOPS, 10 mM $MgCl_2$, 1 mM EDTA, 0.015% Brij-35, 0.1 mg/ml BSA, 0.0025% Beta-Mercaptoethanol). The recombinant enzyme is added to the assay plate containing test compound and the reaction is initiated with a substrate solution containing a final concentration of 0.1 mg/ml PGT, 30 uM ATP, and 0.008 mCi/ml $^{33}$P-gammaATP (3000 Ci/mmol). After a 1 hour incubation at 30° C., the reaction is terminated with 10% TCA and incubated at 4° C. for 1 hour. The reaction is filtered onto a Unifilter® GF/C™ filter plate that has been presoaked with 0.1 M NaPyrophosphate. Microscint-20 is then added to the dried filter plate and the captured $^{33}$P-phosphorylated PGT is quantitated on a microscintillation plate counter (TopCount·NXT™). Inhibition of the kinase enzymatic activity by the test compound is detected by a reduction in scintillation, and the concentration of compound that is required to inhibit the signal by 50% is reported as the $IC_{50}$ value for the test compound.

TrkB

The ability of compounds of the invention to inhibit tyrosine kinase activity of TrkB may be measured using a recombinant enzyme in an assay that measures the ability of compounds to inhibit the phosphorylation of the exogenous substrate, polyGluTyr (PGT, 4:1). The kinase domain of the human TrkB receptor (amino acids 526-838) is expressed in insect cells as a histidine (His)-fusion protein and is commercially available from Invitrogen™. The enzyme assay is performed in a 96-well plate. Test compounds are first dissolved in dimethylsulfoxide (DMSO) and then serially-diluted in a 96-well plate. The serially-diluted compounds are transferred to the 96-well assay plate so that the final concentration of DMSO in the enzyme assay is 1.64%. All assay components are diluted in phosphorylation buffer (20 mm MOPS, 10 mM $MgCl_2$, 1 mM EDTA, 0.015% Brij-35, 0.1 mg/ml BSA, 0.0025% Beta-Mercaptoethanol). The recombinant enzyme is added to the assay plate containing test compound and the reaction is initiated with a substrate solution containing a final concentration of 0.1 mg/ml PGT, 30 uM ATP, and 0.008 mCi/ml $^{33}$P-gammaATP (3000 Ci/mmol)(Perkin Elmer™) After a 1 hour incubation at 30° C., the reaction is terminated with 10% TCA and incubated at 4° C. for 1 hour. The reaction is filtered onto a Unifilter® GF/C™ filter plate that has been presoaked with 0.1 M NaPyrophosphate. Microscint-20 is then added to the dried filter plate and the captured $^{33}$P-phosphorylated PGT is quantitated on a microscintillation plate counter (TopCount·NXT™). Inhibition of the kinase enzymatic activity by the test compound is detected by a reduction in scintillation, and the concentration of compound that is required to inhibit the signal by 50% is reported as the $IC_{50}$ value for the test compound.

The instant compounds inhibit TrkA and TrkB with $IC_{50}$ values between 0.001 to 10 μM. Preferred compounds have $IC_{50}$ values between 0.001-2.5 μM. More preferred compounds have $IC_{50}$ values between 0.001-0.5 μM. Most preferred compounds have $IC_{50}$ values between 0.001-0.1 μM. Representative compounds are listed in following table.

| Ex. No. | TrkA $IC_{50}$ (μM) | TrkB $IC_{50}$ (μM) |
|---|---|---|
| 1 | <0.001 | 0.001 |
| 9 | 0.002 | <0.001 |
| 33 | 0.002 | 0.001 |
| 37 | 0.017 | 0.036 |
| 46 | <0.001 | 0.001 |
| 61 | 0.021 | 0.008 |
| 63 | 0.009 | 0.015 |
| 67 | 0.003 | 0.001 |

Methods of Preparation

Certain compounds of formula I may generally be prepared according to the following schemes and the knowledge of one skilled in the art.

SCHEME 1

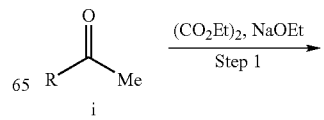

i

-continued

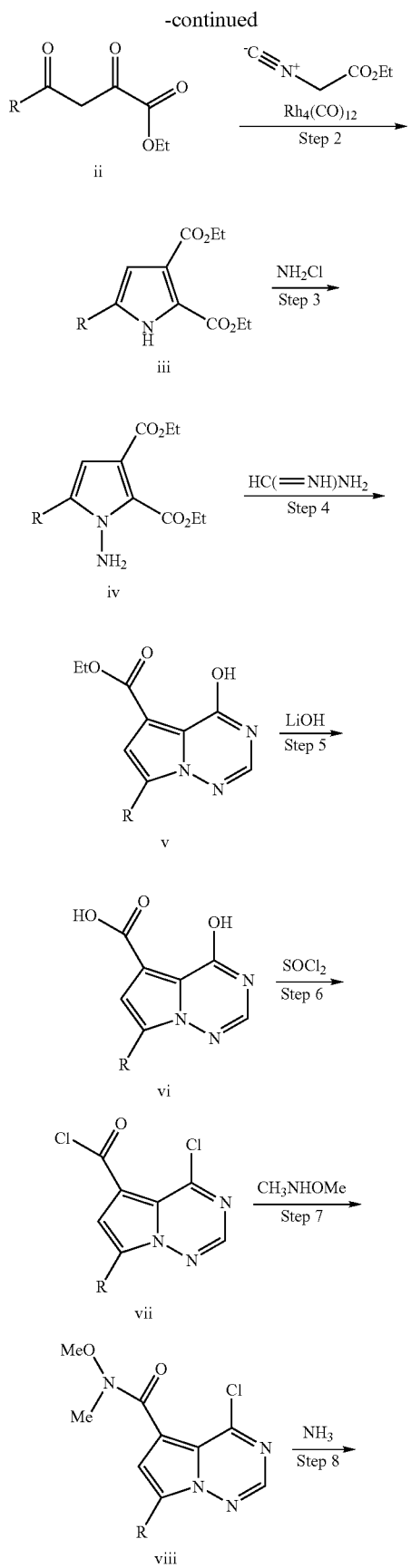

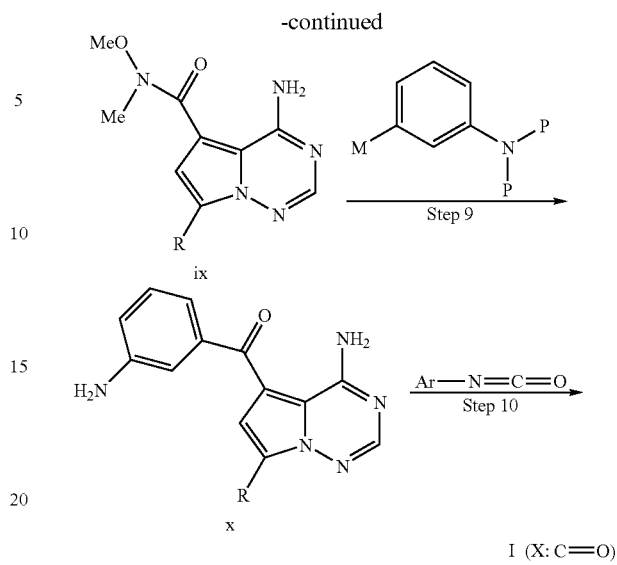

Compound ii was prepared from commercially available Compound i according to known literature procedure (Step 1, Ref.: US 2004/0220186A1). Treatment of Compound ii with ethyl isocyanoacetate in the presence of catalytic amount of rhodium carbonyl complex, $Rh_4(CO)_{12}$, yielded Compound iii (Step 2, Ref.: Shun-Ichi Murahashi et al., *Org. Lett.*, 2001, 3 (3), 421-424). Conversion of Compound iii to Compound iv was accomplished by reacting Compound iii with chloroamine in the presence of a base, such as NaH (Step 3). Reaction of Compound iv with foramidine afforded Compound v (Step 4). Treatment of Compound v with base, such as LiOH, or NaOH, followed by a chlorinating reagent, such as thionyl chloride, gave rise to Compound vii (Step 5 and 6). Compound vii was reacted with N-methyl-N-methoxyamine to give Compound viii (Step 7), which, upon treatment with ammonia, yielded Compound ix (Step 8). Reaction of Compound ix with an anion of a protected aniline, followed by deprotection, provided Compound x (Step 9). Finally, reaction of Compound x with a suitably substituted aryl isocyanate generated Compound I (where X=C=O) (Step 10, Scheme 1).

Alternatively, Compound I can be prepared according to Scheme 2. Compounds xi and xii can be prepared according to known procedure (Step 1, U.S. Ser. No. 09/573829). Conversion of Compound xii to Compound xiii can be achieved by treatment of Compound xii with NBS in the presence of a radical initiator, such as AIBN, or $BzO_2$, followed by aq. $NaHCO_3$ or water (Step 2). Oxidation of Compound xiii to Compound xiv can be achieved by using sodium chlorite (Step 3). Transformations of Compound xiv to Compound xv can be achieved by treatment of xiv with diazomethathane (Step 4). Conversion of Compound xv to xvi is achieved by treatment with ammonia (Step 5). Sequence of Step 4 and Step 5 can be exchanged for optimal yield. Conversion of Compound xvi to xvii is similar to Step 9 in Scheme 1. Conversion of Compound xvii to xviii can be achieved by coupling with acetylene in the presence of a palladium catalyst, or by coupling with substituted boronic acid in the presence of a palladium catalyst (Step 7). Finally, Compound xviii can be further transformed to Compound I according to similar sequences illustrated in Scheme 1.

SCHEME 2

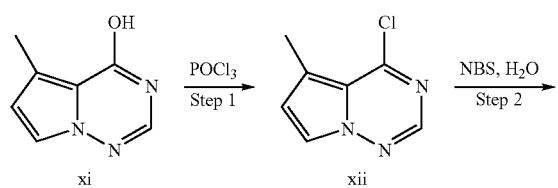

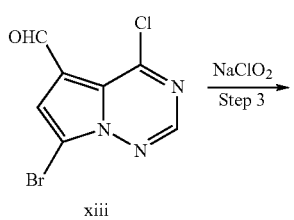

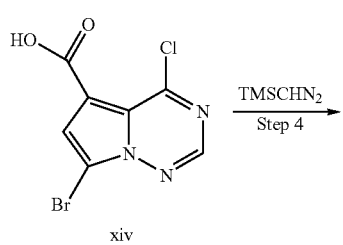

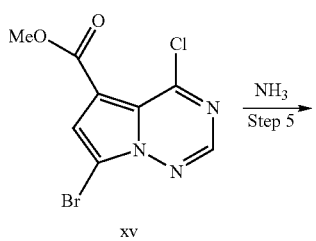

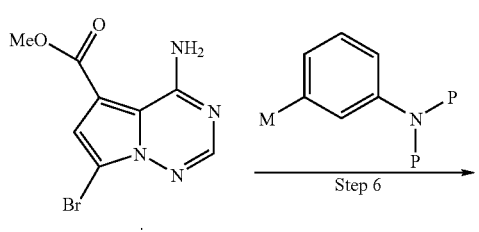

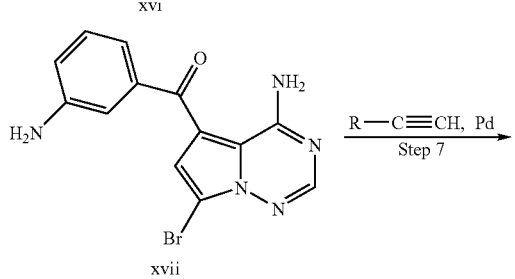

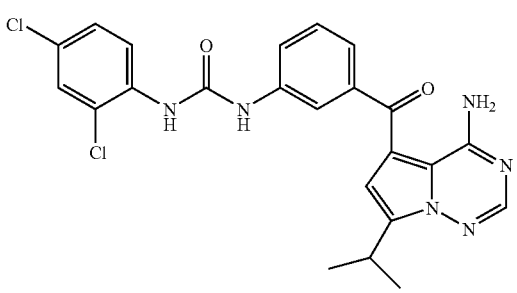

In addition, other compounds of formula I may be prepared using procedures generally known to those skilled in the art. In particular, the following examples provide additional methods for the preparation of the compounds of this invention.

EXAMPLES

The invention will now be further described by the following working example(s), which are preferred embodiments of the invention. All temperatures are in degrees Celsius (° C.) unless otherwise indicated. "HPLC Ret Time" is the HPLC retention time that was obtained under the following conditions: column type and length, gradient time [unless otherwise indicated, all gradients started with 100% solvent A (10% MeOH, 90% H$_2$O, 0.1% TFA) and ended with 100% solvent B (90% MeOH, 10% H$_2$O, 0.1% TFA)], flow rate (mL/min). UV detection was either conducted at 220 nM or at 254. These examples are illustrative rather than limiting and it is to be understood that there may be other embodiments that fall within the spirit and scope of the invention as defined by the claims appended hereto.

Example 1

1-{3-[(4-amino-7-isopropylpyrrolo[2,1-f][1,2,4]triazin-5-yl)carbonyl]phenyl}-3-(2,4-dichlorophenyl)urea

1A. Preparation of diethyl ethyl 5-methyl-2,4-dioxohexanoate

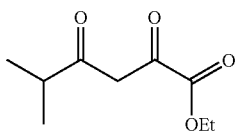
(1A)

Small pieces of sodium (3.39 g, 148 mmol) were dissolved in EtOH (100 ml) under $N_2$ at room temperature and stirred until all the sodium metal dissolved. After the solution cooled down to room temperature, a solution of diethyloxalate (20 ml, 147 mmol) in 3-methyl-2-butanone (18.9 ml, 177 mmol) was added dropwise at room temperature over 30 min. The reaction mixture was then diluted with EtOH (100 ml) and heated at 75° C. for 1.5 h. After cooling to room temperature, the reaction mixture was poured into ice-cold 2 N HCl (200 ml) and extracted with ether (200 ml), followed by EtOAc (100 ml). The combined organic extracts were dried over $MgSO_4$ and concentrated under reduced pressure. The residue was distilled under reduced pressure to give 1A (22.7 g, 83%) as a light yellow oil. $^1$H-NMR ($CDCl_3$) δ:6.41 (2H, s); 4.36 (2 H, q, J=7.14 Hz); 2.67 (1 H, m); 1.37 (3 H, t, J=7.14 Hz); 1.19 (6 H, d, J=7.01 Hz).

1B. Preparation of diethyl 5-isopropyl-1H-pyrrole-2,3-dicarboxylate

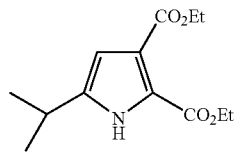
(1B)

A mixture of ethyl isocyanoacetate (18.5 g, 163.7 mmol), 1A (22.1 g, 119 mmol) and $Rh_4(CO)_{12}$ (594 mg, 0.795 mmol) in toluene (50 ml) was degassed and then heated at 80° C. under $N_2$ for 2.5 h. After cooled to room temperature, the reaction mixture was concentrated. The brown oily residue was purified by silica gel column chromatography (hexane/EtOAc=2-20%) to give 1B (15.8 g, 52%) as a light yellow oil. Compound 1B had an analytical HPLC retention time=2.875 min. (Chromolith SpeedROD column 4.6×50 mm, 10-90% aqueous methanol over 4 minutes containing 0.1% TFA, 4 ml/min, monitoring at 220 nm) and a LC/MS $M^++1=254^+$.

1C. Preparation of diethyl 1-amino-5-isopropyl-1H-pyrrole-2,3-dicarboxylate

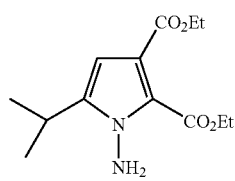
(1C)

To a mixture of $NH_4Cl$ (6.0 g, 109.9 mmol) in $Et_2O$ (220 ml) at −10° C. was added $NH_4OH$ (28-30%, 9.4 ml), followed by dropwise addition of Clorox (144 ml) at −10° C. The mixture was stirred at 0° C. for 1 h. Ether layer was separated and dried over $CaCl_2$. The filtered chloramine ether solution was directly used in the following reaction.

To a solution of 1B (2.53 g, 10 mmol) in dry DMF (40 ml) was added NaH (60%, 550 mg, 13.75 mmol) in one portion. After $H_2$ evolution subsided, $NH_2Cl$ in ether (85 ml) was added dropwise via additional funnel. The reaction mixture was stirred at room temperature for 1 h. Water was added, the mixture was extracted with ether (×3), the combined ether layers were washed with brine, dried over $MgSO_4$, concentrated in vacuo to give 1C (2.50 g, 93%) as an oil. Compound 1C had an analytical HPLC retention time=2.893 min. (Chromolith SpeedROD column 4.6×50 mm, 10-90% aqueous methanol over 4 minutes containing 0.1% TFA, 4 ml/min, monitoring at 220 nm) and a LC/MS $M^++1=269^+$.

1D. Preparation of ethyl 4-hydroxy-7-isopropylpyrrolo[1,2-f][1,2,4]triazine-5-carboxylate

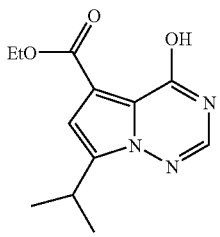
(1D)

A mixture of 1C (13 g, 48.5 mmol) and formamidine acetate (30 g, 0.288 mol) in ethanol (150 ml) was heated at 85° C. overnight. Water was added to the warm reaction mixture and stirred for 30 min. The solid was collected by filtration, washed with water, dried to give 1D (10.5 g, 87%). Compound 1D had an analytical HPLC retention time=2.756 min. (Chromolith SpeedROD column 4.6×50 mm, 10-90% aqueous methanol over 4 minutes containing 0.1% TFA, 4 ml/min, monitoring at 220 nm) and a LC/MS $M^++1=250^+$.

1E. Preparation of 4-hydroxy-7-isopropylpyrrolo[1,2-f][1,2,4]triazine-5-carboxylic acid

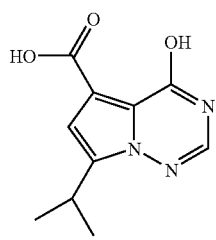
(1E)

To a solution of 1D (9.49 g, 38.1 mmol) in a mixture of THF-MeOH—$H_2O$ (50 ml:50 ml:25 ml) was added $LiOH.H_2O$ (4.8 g, 114.3 mmol). The reaction mixture was heated to reflux for 1 h. After cooling to room temperature, the reaction mixture was concentrated to the volume of about 30 ml and acidified with 2N HCl. The solid was collected by filtration, dried under vacuum to give 1E (8.12 g, 96%). Compound 1E had an analytical HPLC retention time=2.13 min. (Chromolith SpeedROD column 4.6×50 mm, 10-90% aqueous methanol over 4 minutes containing 0.1% TFA, 4 ml/min, monitoring at 220 nm) and a LC/MS $M^++1=222^+$.

1F. Preparation of 4chloro-7-isopropyl-N-methoxy-N-methylpyrrolo[1,2-f][1,2,4]triazine-5-carboxamide

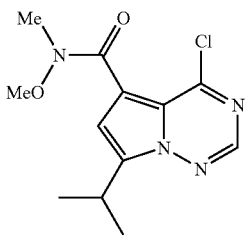

(1F)

To a mixture of 1E (8.12 g, 36.74 mmol) in thionyl chloride (60 ml) was added 5 drops of DMF. The reaction mixture was heated at 80° C. for 5 h. After cooled to room temperature, the reaction mixture was concentrated and azeotropically evaporated twice with dry $CH_2Cl_2$ to give a solid. The solid was dissolved in $CH_2Cl_2$ (100 ml), N-methyl-N-methoxyamine hydrochloride (3.58 g, 36.74 mmol) and $Et_3N$ (15.4 ml, 110.2 mmol) were added subsequently at 0° C. The reaction mixture was stirred at 0° C. for 1 h and diluted with $CH_2Cl_2$, washed with cold 10% citric acid, aq. $NaHCO_3$ and brine, dried over anhydrous $MgSO_4$. After filtration and concentration in vacuo, the residue was purified by silica gel column chromatography (ISCO, hexane/EtOAc 5-100%) to give 1F (7.5 g, 72%) as an oil. Compound 1F had an analytical HPLC retention time=2.375 min. (Chromolith SpeedROD column 4.6×50 mm, 10-90% aqueous methanol over 4 minutes containing 0.1% TFA, 4 ml/min, monitoring at 220 nm) and a LC/MS $M^++1=283^+$.

1G. Preparation of 4-amino-7-isopropyl-N-methoxy-N-methylpyrrolo[1,2-f][1,2,4]triazine-5-carboxamide

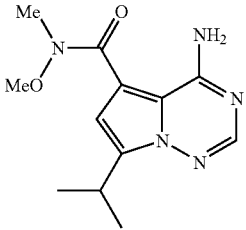

(1G)

A solution of 1F (5.2 g, 18.4 mmol), $NH_4OH$ (60 ml) in dioxane (60 ml) was heated at 55° C. in a sealed reaction vessel for 30 min. After cooled to room temperature the reaction mixture was concentrated under reduced pressure to a smaller volume and the light yellow solid was collected by filtration, washed with water and dried under high vacuum to give 1G (4.46 g, 92%). Compound 1G had an analytical HPLC retention time=2.185 min. (Chromolith SpeedROD column 4.6×50 mm, 10-90% aqueous methanol over 4 minutes containing 0.1% TFA, 4 ml/min, monitoring at 220 nm) and a LC/MS $M^++1=264^+$.

1H. Preparation of (4-amino-7-isopropylpyrrolo[1,2-f][1,2,4]triazin-5-yl)(3-aminophenyl)methanone

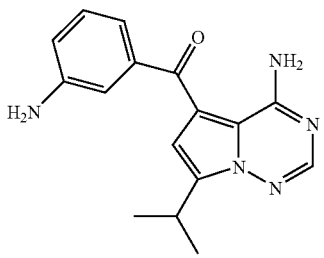

(1H)

To a solution of 1G (1.05 g, 4 mmol) in THF (30 ml) was added 3-[bis(trimethyl-silyl)amino]phenylmagnesium chloride (1.0 M in THF, 49 ml, 49 mmol) dropwise at 0° C. The reaction mixture was stirred at ambient temperature for 2 h, then quenched with saturated aq. $NH_4Cl$. Water was added to dissolve solid and the organic layer was separated, the aqueous layer was extracted with EtOAC (×2). The combined organic layers were washed with brine, dried over anhydrous $MgSO_4$ and concentrated in vacuo. The solid residue was triturated with hexane and the white solid was collected by filtration, rinsed with hexane and dried under vacuum to give 1H (1.16 g, 98%). Compound 1H had an analytical HPLC retention time=1.963 min. (Chromolith SpeedROD column 4.6×50 mm, 10-90% aqueous methanol over 4 minutes containing 0.1% TFA, 4 ml/min, monitoring at 220 nm) and a LC/MS $M^++1=296^+$.

1I. Preparation of 1-{3-[(4-amino-7-isopropylpyrrolo[2,1-f][1,2,4]triazin-5-yl)carbonyl]phenyl}-3-(2,4-dichlorophenyl)urea

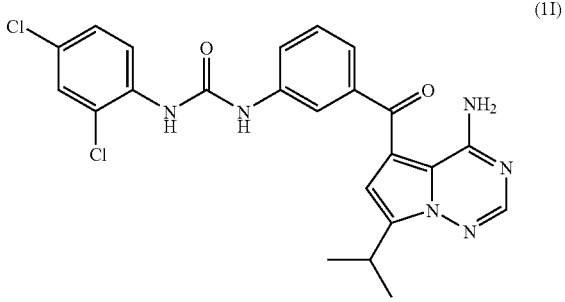

(1I)

Compound 1H (1.12 g, 3.80 mmol) was dissolved in MeOH (30 ml) containing TFA (10 drops) and stirred briefly for 5 min, concentrated and dried under high vacuum. The residue was dissolved in dry acetonitrile (40 ml), 2,6-dichlorophenyl isocyanate (714 mg, 3.80 mmol) was added in one portion. The reaction mixture was stirred at RT for 30 min and concentrated to dryness. The solid was triturated with small amount of $CH_2Cl_2$-MeOH and collected by filtration, rinsed with more MeOH, followed by hexane and dried under high vacuum to give 1I (1.31 g, 72%) as a solid. Compound 1I had an analytical HPLC retention time=3.956 min. (Chromolith SpeedROD column 4.6×50 mm, 10-90% aqueous methanol over 4 minutes containing 0.1% TFA, 4 ml/min, monitoring at 220 nm) and a LC/MS $M^++1=483^+$.

Examples 2 to 63

Examples 2 to 63 were prepared from Compound 1H and corresponding aryl isocyanates utilizing procedure analogous to the one for Compound 1I described above. The final products were purified by trituration, or recrystallization, or preparative HPLC (C18 reverse-phase, YMC ODS S5, 5μm, 20×100 mm, using H2O-MeOH-0.1% TFA as eluents).

| Ex# | R | Name | [M + H]+ | HPLC Ret Time (min) |
|---|---|---|---|---|
| 2 | 2-chlorophenyl (o-Cl) | 1-{3-[(4-amino-7-isopropyl-pyrrolo[2,1-f][1,2,4]triazin-5-yl)carbonyl]phenyl}-3-(2-chloro-5-methylphenyl)urea | 463 | 3.800[a] |
| 3 | 2-chlorophenyl | 1-{3-[(4-amino-7-isopropyl-pyrrolo[2,1-f][1,2,4]triazin-5-yl)carbonyl]phenyl}-3-(2-chlorophenyl)urea | 449 | 3.623[a] |
| 4 | 3,5-dichlorophenyl | 1-{3-[(4-amino-7-isopropyl-pyrrolo[2,1-f][1,2,4]triazin-5-yl)carbonyl]phenyl}-3-(3,5-dichlorophenyl)urea | 483 | 4.01[a] |
| 5 | 3-chlorophenyl | 1-{3-[(4-amino-7-isopropyl-pyrrolo[2,1-f][1,2,4]triazin-5-yl)carbonyl]phenyl}-3-(3-chlorophenyl)urea | 449 | 3.64[a] |
| 6 | 2,4-difluorophenyl | 1-{3-[(4-amino-7-isopropyl-pyrrolo[2,1-f][1,2,4]triazin-5-yl)carbonyl]phenyl}-3-(2,4-difluorophenyl)urea | 451 | 3.52[a] |
| 7 | 2-fluoro-5-methylphenyl | 1-{3-[(4-amino-7-isopropyl-pyrrolo[2,1-f][1,2,4]triazin-5-yl)carbonyl]phenyl}-3-(2-fluoro-5-methylphenyl)urea | 447 | 3.66[a] |

-continued

| Ex# | R | Name | [M + H]+ | HPLC Ret Time (min) |
|---|---|---|---|---|
| 8 | 2,6-difluorophenyl | 1-{3-[(4-amino-7-isopropyl-pyrrolo[2,1-f][1,2,4]triazin-5-yl)carbonyl]phenyl}-3-(2,6-difluorophenyl)urea | 451 | 3.05[a] |
| 9 | phenyl | 1-{3-[(4-amino-7-isopropyl-pyrrolo[2,1-f][1,2,4]triazin-5-yl)carbonyl]phenyl}-3-phenylurea | 415 | 4.16[b] |
| 10 | cyclohexyl | 1-{3-[(4-amino-7-isopropyl-pyrrolo[2,1-f][1,2,4]triazin-5-yl)carbonyl]phenyl}-3-cyclohexylurea | 421 | 3.58[b] |
| 11 | 4-methylbenzyl | 1-{3-[(4-amino-7-isopropyl-pyrrolo[2,1-f][1,2,4]triazin-5-yl)carbonyl]phenyl}-3-(4-methylbenzyl)urea | 443 | 3.64[b] |
| 12 | 2-fluorophenyl | 1-{3-[(4-amino-7-isopropyl-pyrrolo[2,1-f][1,2,4]triazin-5-yl)carbonyl]phenyl}-3-(2-fluorophenyl)urea | 433 | 3.65[c] |
| 13 | 2,6-dichlorophenyl | 1-{3-[(4-amino-7-isopropyl-pyrrolo[2,1-f][1,2,4]triazin-5-yl)carbonyl]phenyl}-3-(2,6-dichlorophenyl)urea | 483 | 3.72[c] |
| 14 | 2-methoxyphenyl | 1-{3-[(4-amino-7-isopropyl-pyrrolo[2,1-f][1,2,4]triazin-5-yl)carbonyl]phenyl}-3-(2-methoxyphenyl)urea | 445 | 3.46[c] |
| 15 | 2-(trifluoromethyl)phenyl | 1-{3-[(4-amino-7-isopropyl-pyrrolo[2,1-f][1,2,4]triazin-5-yl)carbonyl]phenyl}-3-[2-(trifluoromethyl)phenyl]urea | 483 | 3.74[c] |

-continued

| Ex# | R | Name | [M + H]⁺ | HPLC Ret Time (min) |
|---|---|---|---|---|
| 16 | 2-methylphenyl | 1-{3-[(4-amino-7-isopropyl-pyrrolo[2,1-f][1,2,4]triazin-5-yl)carbonyl]phenyl}-3-(2-methylphenyl)urea | 429 | 4.06$^c$ |
| 17 | 3-methoxyphenyl (MeO) | 1-{3-[(4-amino-7-isopropyl-pyrrolo[2,1-f][1,2,4]triazin-5-yl)carbonyl]phenyl}-3-(3-methoxyphenyl)urea | 445 | 3.90$^c$ |
| 18 | 3-methylphenyl | 1-{3-[(4-amino-7-isopropyl-pyrrolo[2,1-f][1,2,4]triazin-5-yl)carbonyl]phenyl}-3-(3-methylphenyl)urea | 429 | 3.63$^c$ |
| 19 | 4-fluorophenyl | 1-{3-[(4-amino-7-isopropyl-pyrrolo[2,1-f][1,2,4]triazin-5-yl)carbonyl]phenyl}-3-(4-fluorophenyl)urea | 433 | 3.76$^c$ |
| 20 | 3-(trifluoromethyl)phenyl (F₃C) | 1-{3-[(4-amino-7-isopropyl-pyrrolo[2,1-f][1,2,4]triazin-5-yl)carbonyl]phenyl}-3-[3-(trifluoromethyl)phenyl]urea | 483 | 3.95$^b$ |
| 21 | 3-chloro-4-fluorophenyl | 1-{3-[(4-amino-7-isopropyl-pyrrolo[2,1-f][1,2,4]triazin-5-yl)carbonyl]phenyl}-3-(3-chloro-4-fluorophenyl)urea | 467 | 3.91$^b$ |
| 22 | 4-cyanophenyl (NC) | 1-{3-[(4-amino-7-isopropyl-pyrrolo[2,1-f][1,2,4]triazin-5-yl)carbonyl]phenyl}-3-(4-cyanophenyl)urea | 440 | 3.91$^b$ |
| 23 | 4-(trifluoromethoxy)phenyl (F₃CO) | 1-{3-[(4-amino-7-isopropyl-pyrrolo[2,1-f][1,2,4]triazin-5-yl)carbonyl]phenyl}-3-[4-(trifluoromethoxy)phenyl]urea | 499 | 3.63$^b$ |

-continued

| Ex# | R | Name | [M + H]⁺ | HPLC Ret Time (min) |
|---|---|---|---|---|
| 24 | PhO-C₆H₄- | 1-{3-[(4-amino-7-isopropyl-pyrrolo[2,1-f][1,2,4]triazin-5-yl)carbonyl]phenyl}-3-(4-phenoxyphenyl)urea | 507 | 3.95[b] |
| 25 | 2,4-dimethylphenyl | 1-{3-[(4-amino-7-isopropyl-pyrrolo[2,1-f][1,2,4]triazin-5-yl)carbonyl]phenyl}-3-(2,4-dimethylphenyl)urea | 443 | 3.99[b] |
| 26 | 1-naphthyl | 1-{3-[(4-amino-7-isopropyl-pyrrolo[2,1-f][1,2,4]triazin-5-yl)carbonyl]phenyl}-3-(1-naphthyl)urea | 465 | 3.76[b] |
| 27 | 4-F₃C-C₆H₄- | 1-{3-[(4-amino-7-isopropyl-pyrrolo[2,1-f][1,2,4]triazin-5-yl)carbonyl]phenyl}-3-[4-(trifluoromethyl)phenyl]urea | 483 | 3.79[b] |
| 28 | 4-Cl-C₆H₄- | 1-{3-[(4-amino-7-isopropyl-pyrrolo[2,1-f][1,2,4]triazin-5-yl)carbonyl]phenyl}-3-(4-chlorophenyl)urea | 449 | 3.96[b] |
| 29 | 4-Br-C₆H₄- | 1-{3-[(4-amino-7-isopropyl-pyrrolo[2,1-f][1,2,4]triazin-5-yl)carbonyl]phenyl}-3-(4-bromophenyl)urea | 493 | 3.87[b] |
| 30 | 5-fluoro-2-methylphenyl | 1-{3-[(4-amino-7-isopropyl-pyrrolo[2,1-f][1,2,4]triazin-5-yl)carbonyl]phenyl}-3-(5-fluoro-2-methylphenyl)urea | 447 | 3.92[b] |

-continued

| Ex# | R | Name | [M + H]+ | HPLC Ret Time (min) |
|---|---|---|---|---|
| 31 | 3-methylbenzyl | 1-{3-[(4-amino-7-isopropyl-pyrrolo[2,1-f][1,2,4]triazin-5-yl)carbonyl]phenyl}-3-(3-methylbenzyl)urea | 443 | 3.79[b] |
| 32 | 4-(dimethylamino)phenyl | 1-{3-[(4-amino-7-isopropyl-pyrrolo[2,1-f][1,2,4]triazin-5-yl)carbonyl]phenyl}-3-[4-(dimethylamino)phenyl]urea | 458 | 3.65[b] |
| 33 | BnO-(4-phenyl) | 1-{3-[(4-amino-7-isopropyl-pyrrolo[2,1-f][1,2,4]triazin-5-yl)carbonyl]phenyl}-3-[4-(benzyloxy)phenyl]urea | 521 | 2.85[b] |
| 34 | t-Bu-(4-phenyl) | 1-{3-[(4-amino-7-isopropyl-pyrrolo[2,1-f][1,2,4]triazin-5-yl)carbonyl]phenyl}-3-(4-tert-butylphenyl)urea | 471 | 3.93[b] |
| 35 | Ph-(4-phenyl) | 1-{3-[(4-amino-7-isopropyl-pyrrolo[2,1-f][1,2,4]triazin-5-yl)carbonyl]phenyl}-3-biphenyl-4-yl-urea | 491 | 4.05[b] |
| 36 | tert-butyl | 1-{3-[(4-amino-7-isopropyl-pyrrolo[2,1-f][1,2,4]triazin-5-yl)carbonyl]phenyl}-3-tert-butylurea | 395 | 4.03[b] |
| 37 | cyclohexylmethyl | 1-{3-[(4-amino-7-isopropyl-pyrrolo[2,1-f][1,2,4]triazin-5-yl)carbonyl]phenyl}-3-(cyclohexylmethyl)urea | 435 | 3.49[b] |
| 38 | 2,3-dichlorophenyl | 1-{3-[(4-amino-7-isopropyl-pyrrolo[2,1-f][1,2,4]triazin-5-yl)carbonyl]phenyl}-3-(2,3-dichlorophenyl)urea | 483 | 4.11[b] |

-continued

| Ex# | R | Name | [M + H]⁺ | HPLC Ret Time (min) |
|---|---|---|---|---|
| 39 | 4-methoxyphenyl | 1-{3-[(4-amino-7-isopropyl-pyrrolo[2,1-f][1,2,4]triazin-5-yl)carbonyl]phenyl}-3-(4-methoxyphenyl)urea | 445 | 3.53$^b$ |
| 40 | 4-methylphenyl | 1-{3-[(4-amino-7-isopropyl-pyrrolo[2,1-f][1,2,4]triazin-5-yl)carbonyl]phenyl}-3-(4-methylphenyl)urea | 429 | 3.75$^b$ |
| 41 | (1S)-1-phenylethyl | 1-{3-[(4-amino-7-isopropyl-pyrrolo[2,1-f][1,2,4]triazin-5-yl)carbonyl]phenyl}-3-[(1S)-1-phenylethyl]urea | 443 | 3.57$^b$ |
| 42 | benzyl | 1-{3-[(4-amino-7-isopropyl-pyrrolo[2,1-f][1,2,4]triazin-5-yl)carbonyl]phenyl}-3-benzylurea | 429 | 3.50$^b$ |
| 43 | 2,5-difluorophenyl | 1-{3-[(4-amino-7-isopropyl-pyrrolo[2,1-f][1,2,4]triazin-5-yl)carbonyl]phenyl}-3-(2,5-difluorophenyl)urea | 451 | 3.95$^b$ |
| 44 | 3,5-dimethylphenyl | 1-{3-[(4-amino-7-isopropyl-pyrrolo[2,1-f][1,2,4]triazin-5-yl)carbonyl]phenyl}-3-(3,5-dimethylphenyl)urea | 443 | 3.92$^b$ |
| 45 | 2-methoxy-5-methylphenyl | 1-{3-[(4-amino-7-isopropyl-pyrrolo[2,1-f][1,2,4]triazin-5-yl)carbonyl]phenyl}-3-(2-methoxy-5-methylphenyl)urea | 459 | 3.92$^b$ |
| 46 | 2-naphthyl | 1-{3-[(4-amino-7-isopropyl-pyrrolo[2,1-f][1,2,4]triazin-5-yl)carbonyl]phenyl}-3-(2-naphthyl)urea | 465 | 3.93$^b$ |

-continued

| Ex# | R | Name | [M + H]⁺ | HPLC Ret Time (min) |
|---|---|---|---|---|
| 47 | (2-phenylethyl) | 1-{3-[(4-amino-7-isopropyl-pyrrolo[2,1-f][1,2,4]triazin-5-yl)carbonyl]phenyl}-3-(2-phenylethyl)urea | 443 | 3.61$^b$ |
| 48 | (3-fluoro-4-methylphenyl) | 1-{3-[(4-amino-7-isopropyl-pyrrolo[2,1-f][1,2,4]triazin-5-yl)carbonyl]phenyl}-3-(3-fluoro-4-methylphenyl)urea | 447 | 3.87$^b$ |
| 49 | (biphenyl-2-yl) | 1-{3-[(4-amino-7-isopropyl-pyrrolo[2,1-f][1,2,4]triazin-5-yl)carbonyl]phenyl}-3-biphenyl-2-ylurea | 491 | 3.93$^b$ |
| 50 | [(1R)-1-phenylethyl] | 1-{3-[(4-amino-7-isopropyl-pyrrolo[2,1-f][1,2,4]triazin-5-yl)carbonyl]phenyl}-3-[(1R)-1-phenylethyl]urea | 443 | 3.57$^b$ |
| 51 | (3,4-difluorophenyl) | 1-{3-[(4-amino-7-isopropyl-pyrrolo[2,1-f][1,2,4]triazin-5-yl)carbonyl]phenyl}-3-(3,4-difluorophenyl)urea | 451 | 3.85$^b$ |
| 52 | methyl (2S)-3-methylbutanoate | methyl (2S)-2-[({3-[(4-amino-7-isopropylpyrrolo[2,1-f][1,2,4]triazin-5-yl)carbonyl]phenyl}carbamoyl)amino]-3-methylbutanoate | 453 | 3.44$^b$ |
| 53 | methyl (2S)-4-methylpentanoate | methyl (2S)-2-[({3-[(4-amino-7-isopropylpyrrolo[2,1-f][1,2,4]triazin-5-yl)carbonyl]-phenyl}carbamoyl)-amino]-4-methylpentanoate | 467 | 3.59$^b$ |

-continued

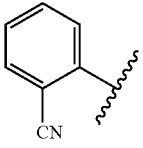

| Ex# | R | Name | [M + H]+ | HPLC Ret Time (min) |
|---|---|---|---|---|
| 54 | 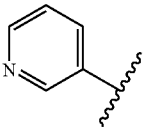 | 1-{3-[(4-amino-7-isopropyl-pyrrolo[2,1-f][1,2,4]triazin-5-yl)carbonyl]phenyl}-3-(2-cyanophenyl)urea | 440 | 3.59[b] |
| 55 | 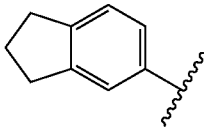 | 1-{3-[(4-amino-7-isopropyl-pyrrolo[2,1-f][1,2,4]triazin-5-yl)carbonyl]phenyl}-3-pyridin-3-ylurea | 416 | 2.73[b] |
| 56 | 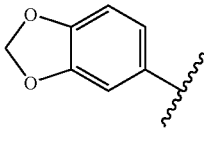 | 1-{3-[(4-amino-7-isopropyl-pyrrolo[2,1-f][1,2,4]triazin-5-yl)carbonyl]phenyl}-3-(2,3-dihydro-1H-inden-5-yl)urea | 455 | 3.93[b] |
| 57 | 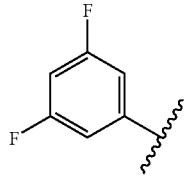 | 1-{3-[(4-amino-7-isopropyl-pyrrolo[2,1-f][1,2,4]triazin-5-yl)carbonyl]phenyl}-3-(1,3-benzodioxol-5-yl)urea | 459 | 3.55[b] |
| 58 | 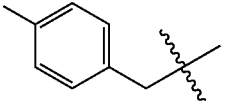 | 1-{3-[(4-amino-7-isopropyl-pyrrolo[2,1-f][1,2,4]triazin-5-yl)carbonyl]phenyl}-3-(3,5-difluorophenyl)urea | 451 | 3.93[b] |
| 59 | 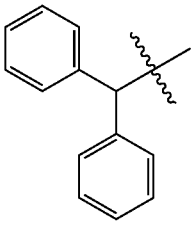 | 1-{3-[(4-amino-7-isopropyl-pyrrolo[2,1-f][1,2,4]triazin-5-yl)carbonyl]phenyl}-3-(4-chlorobenzyl)urea | 463 | 3.74[b] |
| 60 | | 1-{3-[(4-amino-7-isopropyl-pyrrolo[2,1-f][1,2,4]triazin-5-yl)carbonyl]phenyl}-3-(diphenylmethyl)urea | 505 | 3.82[b] |

-continued

| Ex# | R | Name | [M + H]+ | HPLC Ret Time (min) |
|---|---|---|---|---|
| 61 | (3-phenylpropyl group) | 1-{3-[(4-amino-7-isopropyl-pyrrolo[2,1-f][1,2,4]triazin-5-yl)carbonyl]phenyl}-3-(3-phenylpropyl)urea | 457 | 3.74[b] |
| 62 | (pyridin-2-yl group) | 1-{3-[(4-amino-7-isopropyl-pyrrolo[2,1-f][1,2,4]triazin-5-yl)carbonyl]phenyl}-3-pyridin-2-ylurea | 416 | 2.82[b] |
| 63 | (pyridin-4-yl group) | 1-{3-[(4-amino-7-isopropyl-pyrrolo[2,1-f][1,2,4]triazin-5-yl)carbonyl]phenyl}-3-pyridin-4-ylurea | 416 | 2.625[a] |

HPLC and LC-MS analysis conditions:
[a]Method A: Chromolith SpeedROD 4.6 x 50 mm, 5 5 μm column;
[b]Method B: Phenomenex Luna C18 (2), 4.6 x 50 mm, 5 5 μm column;
[c]Method C: Waters SunFire C18, 4.6 x 50 mm, 5 μm column.

Example 64 p-tolyl 3-(4-amino-7-isopropylpyrrolo[1,2-f][1,2,4]triazine-5-carbonyl) phenylcarbamate

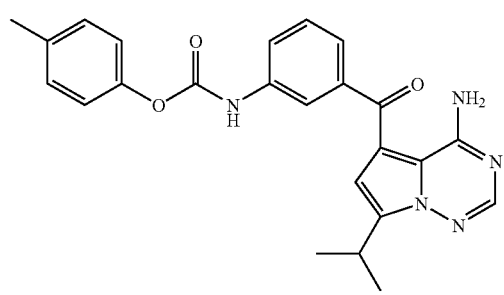

Example 64 was prepared from Compound 1H and 4-methylphenyl chloro-formate in the presence of triethyl amine utilizing procedure analogous to the one for Compound 1I described above. The final products were purified by preparative HPLC (C18 reverse-phase, YMC ODS S5, 5μm, 20×100 mm, using H2O-MeOH-0.1% TFA as eluents). Compound 64 had an analytical HPLC retention time=3.571 min. (Chromolith SpeedROD column 4.6×50 mm, 10-90% aqueous methanol over 4 minutes containing 0.1% TFA, 4 ml/min, monitoring at 220 nm) and a LC/MS M++1=430+.

Example 65

1-{3-[(4-amino-7-isopropyl-pyrrolo[2,1-f][1,2,4]triazin-5-yl)carbonyl]phenyl}-3-piperidin-4-ylurea

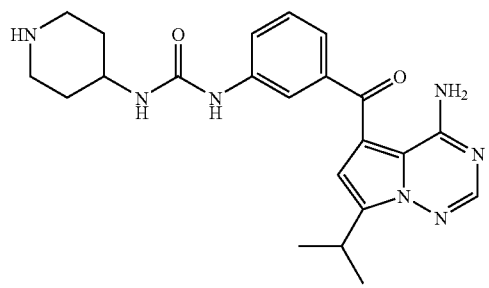

65A Preparation of 65A

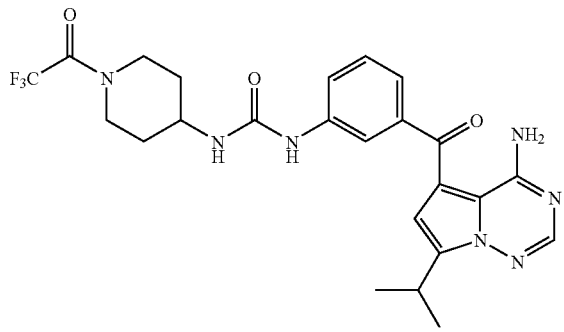

65A

Compound 65A was prepared from Compound 1H (30 mg, 0.0733 mmol) and 2,2,2-trifluoro-1-(4-isocyanatopiperidin-1-yl)ethanone (16.3 mg, 0.0733 mmol) utilizing procedure analogous to the one for Compound 1I described above. The compound was purified by preparative HPLC and had an analytical HPLC retention time=3.160 min. (Chromolith SpeedROD column 4.6×50 mm, 10-90% aqueous methanol over 4 minutes containing 0.1% TFA, 4 ml/min, monitoring at 220 nm) and a LC/MS $M^+ +1=518^+$.

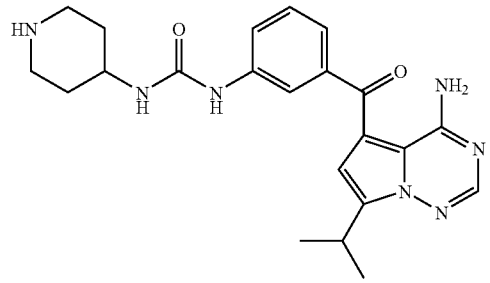

To a solution of 65A in MeOH (1 ml) was added 1 N NaOH (0.2 ml). The mixture was stirred at rt for 30 min. Preparative HPLC purification gave the TFA salt of 65B (8.2 mg, 27% for two steps) as a solid. It had an analytical HPLC retention time=2.420 min. (Chromolith SpeedROD column 4.6×50 mm, 10-90% aqueous methanol over 4 minutes containing 0.1% TFA, 4 ml/min, monitoring at 220 nm) and a LC/MS $M^+ +1=422^+$.

Example 66

1-(3-(4-amino-7-(3-(dimethylamino)prop-1-ynyl)pyrrolo[1,2-f][1,2,4]triazine-5-carbonyl)phenyl)-3-(2,4-dichlorophenyl)urea

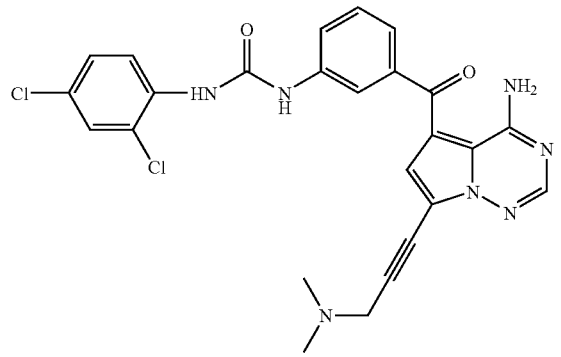

66A. Preparation of 7-bromo-4-chloropyrrolo[1,2-f][1,2,4]triazine-5-carbaldehyde

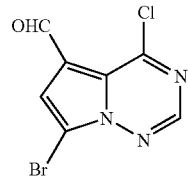

To a solution of 4-chloro-5-methylpyrrolo[1,2-f][1,2,4]triazine (168 mg, 1 mmol) in $CCl_4$ (5 ml) was added NBS (0.82 g, 5 mmol) and AIBN (18 mg, 0.1 mmol). The mixture was degassed, and then heated at reflux under $N_2$ for 5 h. Cooled to RT. EtOAc and aq. $NaHCO_3$ were added, and the mixture was stirred at RT for 2 h. The organic layer was separated, washed with brine, dried and concentrated. The residue was purified by ISCO silica gel column (EtOAc-hexane 0-30%) to give 66A (85 mg, 33%) as a solid. Compound 66A had an analytical HPLC retention time=2.003 min. (Chromolith SpeedROD column 4.6×50 mm, 10-90% aqueous methanol over 4 minutes containing 0.1% TFA, 4 ml/min, monitoring at 220 nm) and a LC/MS $M^+ +1=256^+$.

66B. Preparation of 7-bromo-4-chloropyrrolo[1,2-f][1,2,4]triazine-5-carboxylic Acid

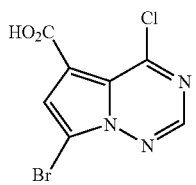

A mixture of 66A (69 mg, 0.226 mmol) in dioxane (5 ml) was added a solution of $NaH_2PO_4.H_2O$ (125 mg, 0.904 mmol) in water (1 ml) and $H_2NSO_3H$ (33 mg, 0.339 mmol). The mixture was cooled to 0° C., a solution of $NaClO_2$ in water (1 ml) was added dropwise. Then the reaction was warmed to rt and stirred for 1 h, $Na_2S_2O_3$ (34 mg, 0.271 mmol) was added and stirred for 15 min. The reaction mixture was acidified with 1 N HCl to pH 3, extracted with EtOAc for three times. The combined extracts was dried to give 66B (60 mg, 96%) as a solid. Compound 66B had an analytical HPLC retention time=2.022 min. (Chromolith SpeedROD column 4.6×50 mm, 10-90% aqueous methanol over 4 minutes containing 0.1% TFA, 4 ml/min, monitoring at 220 nm) and a LC/MS $M^+ +1=276^+$.

66C. Preparation of methyl 7-bromo-4-aminopyrrolo[1,2-f][1,2,4]triazine-5-carboxylate

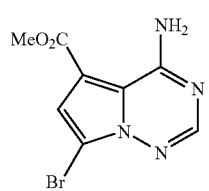

To a solution of 66B (576 mg, 2.08 mmol) in DCM/MeOH (8 ml/8 ml) was added a solution of 2 M TMSCHN$_2$ in hexane (6.24 mmol, 3.12 mmol). The mixture was stirred for 30 min, then concentrated. The resulting solid was dissolved in DCM (5 ml), and a solution of 2 N NH$_3$/MeOH was added. The mixture was stirred for 15 min, then concentrated. The solid was triturated with small amount of DCM, filtered and dried to give 66C (372 mg, 66%) as a solid. Compound 66C had an analytical HPLC retention time=2.262 min. (Chromolith SpeedROD column 4.6×50 mm, 10-90% aqueous methanol over 4 minutes containing 0.1% TFA, 4 ml/min, monitoring at 220 nm) and a LC/MS M$^+$+1=271$^+$.

66D. Preparation of (4-amino-7-bromopyrrolo[1,2-f][1,2,4]triazin-5-yl)(3-amino-phenyl)methanone

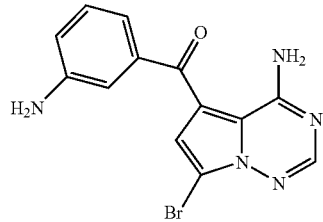

To a mixture of 66C (350 mg, 1.29 mmol) and N-methyl-N-methoxyamine hydrochloride (189 mg, 1.935 mmol) in THF (10 ml) at −10° C. was added 3-[bis(trimethyl-silyl)amino]phenylmagnesium chloride (1.0 M in THF, 21 ml, 21 mmol) dropwise. The reaction was stirred at 0° C. for 2 h, then at rt overnight. The mixture was quenched with saturated aq. NH$_4$Cl. Water was added to dissolve solid and the organic layer was separated and the aqueous layer was extracted with EtOAC (×2). The combined organic layers were washed with brine, dried over anhydrous MgSO$_4$ and concentrated in vacuo. The residue was triturated with hexane and the solid was collected by filtration, rinsed with hexane and dried under vacuum to give 66D (92.8 mg, 22%). Compound 66D had an analytical HPLC retention time=1.663 min. (Chromolith SpeedROD column 4.6×50 mm, 10-90% aqueous methanol over 4 minutes containing 0.1% TFA, 4 ml/min, monitoring at 220 nm) and a LC/MS M$^+$+1=332$^+$.

66E. Preparation of (4-amino-7-(3-(dimethylamino)prop-1-ynyl)pyrrolo[1,2-f]-[1,2,4]triazin-5-yl)(3-aminophenyl)methanone

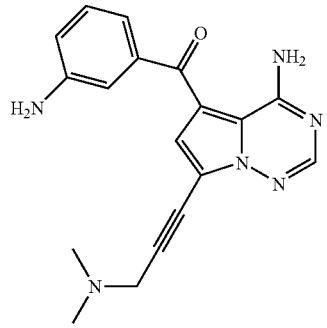

A mixture of 66D (10 mg, 0.03 mmol), propargylamine (3.3 mg, 0.06 mmol), pd(dppf)$_2$Cl$_2$·CH$_2$Cl$_2$ (3 mg, 0.004 mmol), CuI (2 mg, 0.01 mmol) and Et$_3$N (0.1 ml) in THF (0.6 m) was degassed by bubbling in N$_2$, then heated at 70° C. in a vial for 1 h. The mixture was cooled to RT and the residue was purified by preparative HPLC (C18 reverse-phase, YMC ODS S5, 5 μm, 20×100 mm, using H2O-MeOH-0.1% TFA as eluents) to give 66E as the TFA salt, which was directly used in next step reaction. Compound 66E had an analytical HPLC retention time=1.135 min. (Chromolith SpeedROD column 4.6×50 mm, 10-90% aqueous methanol over 4 minutes containing 0.1% TFA, 4 ml/min, monitoring at 220 nm) and a LC/MS M$^+$+1=335$^+$.

66F. Preparation of 1-(3-(4-amino-7-(3-(dimethylamino)prop-1-ynyl)pyrrolo[1,2-f][1,2,4]triazine-5-carbonyl)phenyl)-3-(2,4-dichlorophenyl)urea

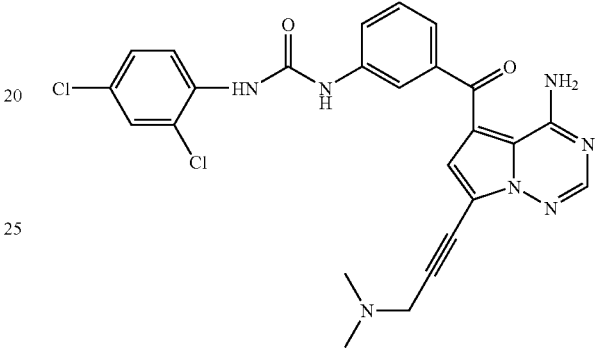

To a solution of the TFA salt of 66E in CH$_3$CN (1 ml) was added dichlorophenyl isocyanate (3.1 mg, 0.0164 mmol). The mixture was stirred at rt for 30 min. Preparative HPLC (C18 reverse-phase, YMC ODS S5, 5μm, 20×100 mm, using H2O-MeOH-0.1% TFA as eluents) gave the title compound 66 (3.4 mg, 18% for two step from 66D) as TFA salt. Compound 66F had an analytical HPLC retention time=3.026 min. (Chromolith SpeedROD column 4.6×50 mm, 10-90% aqueous methanol over 4 minutes containing 0.1% TFA, 4 ml/min, monitoring at 220 nm) and a LC/MS M$^+$+1=522$^+$.

Example 67

1-[3-({4-amino-7-[3-(dimethylamino)propyl]Pyrrolo[2,1-f][1,2,4]triazin-5-yl}carbonyl)phenyl]-3-(2,4-dichlorophenyl)urea

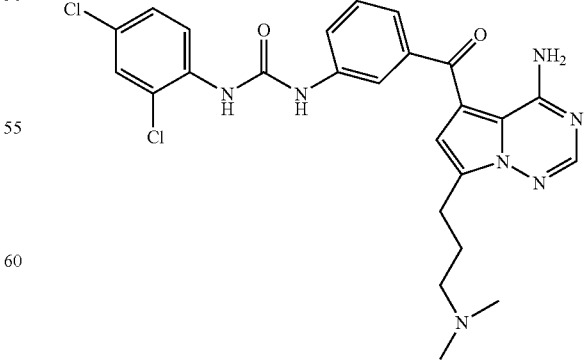

A suspension of Compound 66 (11 mg, 0.02 mmol) and 10% Pd/C (5 mg) in EtOAc (4 mL) was purged with nitrogen (2x) and stirred under an H₂ atmosphere for 3 days. The reaction mixture was filtered and the filtrate was concentrated. The crude product was purified by preparative reversed-phase HPLC and the fractions containing the desired compound were lyophilized to a solid (1.7 mg) as a TFA salt. Compound 67 had an analytical HPLC retention time=2.853 min. (Chromolith SpeedROD column 4.6×50 mm, 10-90% aqueous methanol over 4 minutes containing 0.1% TFA, 4 ml/min, monitoring at 220 nm) and a LC/MS M$^+$+1=526$^+$.

Example 68

1-(5-{[4-amino-7-(1-methylethyl)pyrrolo[2,1-f][1,2,4]triazin-5-yl]carbonyl}-3-pyridinyl)-3-(2,4-dichlorophenyl)urea

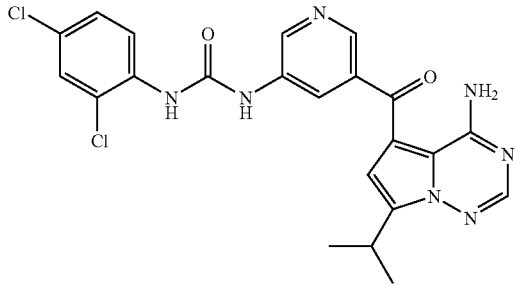

68A. Preparation of tert-butyl 5-bromopyridin-3-ylcarbamate

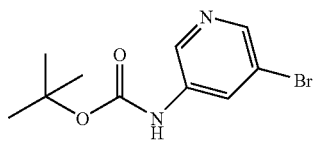

A solution of 5-bromo nicotinic acid (10.0 g, 49.5 mmol) in 1,4-dioxane (70 mL) was treated with diphenylphosphoryl azide (12.8 mL, 59 mmol) and triethylamine (8 mL, 59 mmol) at ambient temperature. The solution was allowed to stir for 30 minutes. t-Butyl alcohol (23 mL) was added and the reaction was heated to 75° C. overnight. After cooling to ambient temperature, the solvent was removed under reduced pressure and the residue was dissolved in EtOAc (100 mL) and washed with water (100 mL), followed by saturated aqueous NaHCO₃ (100 mL) and 1 N HCl (50 mL). The organic layer was dried (Na₂SO₄), filtered and concentrated. The crude bromide was purified by flash chromatography (SiO₂, 0% to 25% MeOH/CH₂Cl₂) to afford the title compound as a solid (4.0 g, 30%). 1H NMR (400 Mz, CDCl₃) δ 9.82 (s, 1H), 8.55 (d, 1H, J=2.27 Hz), 8.28 (d, 1H, J=2.0 Hz), 8.16 (s, 1H), 1.47 (s, 9H). HPLC t$_R$=3.65 min (YMC S5 ODS 4.6×50 mm, 10-90% aqueous methanol containing 0.2% H₃PO₄, 4 min gradient, monitored at 220 nm). [M+H+]=273.17.

68B. Preparation of (4-amino-7-isopropylpyrrolo[1,2-f][1,2,4]triazin-5-yl)(5-aminopyridin-3-yl)methanone

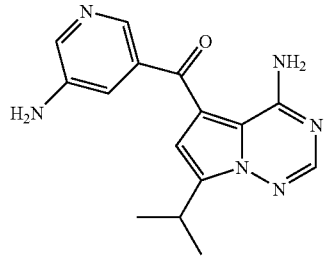

A solution of 68A (250 mg, 0.92 mmol) in THF (5 mL) was cooled to 0° C. A solution of MgBu₂ (1.0 M in heptane, 0.92 mL, 0.92 mmol) was slowly added maintaining the reaction temperature below 5° C. The resulting solution was stirred at 0° C. for one hour then cooled to −78° C. A solution of n-BuLi (1.6 M in hexane, 0.58 mL, 0.92 mmol) was added and the reaction was stirred at −78° C. for 15 minutes. The reaction was warmed to 0° C. and stirred for 30 minutes before a solution of 1G (121 mg, 0.46 mmol) was added. The resulting solution was stirred at ambient temperature for 18 hours and then quenched with saturated aqueous NaCl solution (10 mL). The layers were separated and the aqueous layer was extracted with EtOAc (2×10 mL). The combined organic layers were dried (MgSO₄), then filtered and concentrated. The resulting oil was dissolved in CH₂Cl₂ (10 mL) and treated with TFA (2 mL). The reaction was stirred for 4 hours at room temperature and then concentrated. The crude amine was purified by reversed-phase preparative HPLC (YMC ODS-A 30×250 mm, 10-90% aqueous methanol containing 0.1% TFA, 30 min gradient, monitored at 220 nm). The fractions containing the desired product were lyophilized to afford the title compound as a powder (67 mg, 40%). ). HPLC t$_R$=2.08 min (YMC S5 ODS 4.6×50 mm, 10-90% aqueous methanol containing 0.2% H₃PO₄, 4 min gradient, monitored at 220 nm). [M+H+]=297.28.

68C. Preparation of 1-(5-{[4-amino-7-(1-methylethyl)pyrrolo[2,1-f][1,2,4]triazin-5-yl]carbonyl}-3-pyridinyl)-3-(2,4-dichlorophenyl)urea

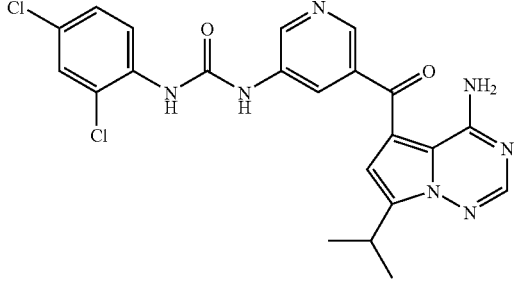

A solution of 68B (197 mg, 0.49 mmol) in pyridine (10 mL) was treated with 2,4-dichloroisocyanate (93 mg, 0.49 mmol) at room temperature. The reaction was stirred for 3 hours, and then concentrated to dryness. The residue was suspended in MeOH (10 mL) and stirred at room temperature. The resulting solid was collected by filtration and dried under vacuum to afford the title compound (220 mg, 93%). HPLC tR=3.756 min (Chromolith SpeedROD 4.6×50 mm, 10-90% aqueous methanol containing 0.1% TFA, 4 min gradient, monitored at 220 nm). [M+H+]=484.12.

Examples 69 to 82

Examples 69 to 82 were prepared from Compound 68B and corresponding aryl isocyanates utilizing procedure analogous to the one for Compound 68 described above. The final products were purified by trituration, or recrystallization, or preparative HPLC (C18 reverse-phase, YMC ODS S5, 5μm, 20×100 mm, using H2O-MeOH-0.1% TFA as eluents).

| Ex# | R | Name | [M + H]$^+$ | HPLC Ret Time (min) |
|---|---|---|---|---|
| 69 | 3-pyridinyl | 1-(5-{[4-amino-7-(1-methylethyl)pyrrolo[2,1-f][1,2,4]triazin-5-yl]carbonyl}-3-pyridinyl)-3-(3-pyridinyl)urea | | |
| 70 | 4-chloro-2-methylphenyl | 1-(5-{[4-amino-7-(1-methylethyl)pyrrolo[2,1-f][1,2,4]triazin-5-yl]carbonyl}-3-pyridinyl)-3-(4-chloro-2-methylphenyl)urea | 464 | 3.44$^a$ |
| 71 | 4-chlorophenyl | 1-(5-{[4-amino-7-(1-methylethyl)pyrrolo[2,1-f][1,2,4]triazin-5-yl]carbonyl}-3-pyridinyl)-3-(4-chlorophenyl)urea | 450 | 3.36$^a$ |
| 72 | 2-fluorophenyl | 1-(5-{[4-amino-7-(1-methylethyl)pyrrolo[2,1-f][1,2,4]triazin-5-yl]carbonyl}-3-pyridinyl)-3-(2-fluorophenyl)urea | 434 | 3.16$^a$ |
| 73 | 2-chlorophenyl | 1-(5-{[4-amino-7-(1-methylethyl)pyrrolo[2,1-f][1,2,4]triazin-5-yl]carbonyl}-3-pyridinyl)-3-(2-chlorophenyl)urea | 450 | 3.37$^a$ |
| 74 | 2,4-difluorophenyl | 1-(5-{[4-amino-7-(1-methylethyl)pyrrolo[2,1-f][1,2,4]triazin-5-yl]carbonyl}-3-pyridinyl)-3-(2,4-difluorophenyl)urea | 452 | 3.16$^a$ |

-continued

| Ex# | R | Name | [M + H]⁺ | HPLC Ret Time (min) |
|---|---|---|---|---|
| 75 | 2-(trifluoromethyl)phenyl | 1-(5-{[4-amino-7-(1-methylethyl)pyrrolo[2,1-f][1,2,4]triazin-5-yl]carbonyl}-3-pyridinyl)-3-[2-(trifluoromethyl)phenyl]urea | 484 | 3.19$^a$ |
| 76 | 2-cyanophenyl | 1-(5-{[4-amino-7-(1-methylethyl)pyrrolo[2,1-f][1,2,4]triazin-5-yl]carbonyl}-3-pyridinyl)-3-(2-cyanophenyl)urea | 441 | 2.93$^a$ |
| 77 | 3-cyanophenyl | 1-(5-{[4-amino-7-(1-methylethyl)pyrrolo[2,1-f][1,2,4]triazin-5-yl]carbonyl}-3-pyridinyl)-3-(3-cyanophenyl)urea | 441 | 3.04$^a$ |
| 78 | 4-cyanophenyl | 1-(5-{[4-amino-7-(1-methylethyl)pyrrolo[2,1-f][1,2,4]triazin-5-yl]carbonyl}-3-pyridinyl)-3-(4-cyanophenyl)urea | 441 | 3.06$^a$ |
| 79 | 1,3-benzodioxol-5-yl | 1-(5-{[4-amino-7-(1-methylethyl)pyrrolo[2,1-f][1,2,4]triazin-5-yl]carbonyl}-3-pyridinyl)-3-(1,3-benzodioxol-5-yl)urea | 460 | 2.96$^a$ |
| 80 | 4-fluorophenyl | 1-(5-{[4-amino-7-(1-methylethyl)pyrrolo[2,1-f][1,2,4]triazin-5-yl]carbonyl}-3-pyridinyl)-3-(4-fluorophenyl)urea | 434 | 3.08$^a$ |
| 81 | 4-(Me)₂N-phenyl | 1-(5-{[4-amino-7-(1-methylethyl)pyrrolo[2,1-f][1,2,4]triazin-5-yl]carbonyl}-3-pyridinyl)-3-[4-(dimethylamino)phenyl]urea | 459 | 2.28$^a$ |

-continued

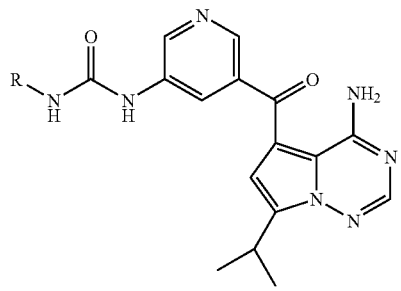

| Ex# | R | Name | [M + H]⁺ | HPLC Ret Time (min) |
|---|---|---|---|---|
| 82 | (2-methoxyphenyl) | 1-(5-{[4-amino-7-(1-methylethyl)pyrrolo[2,1-f][1,2,4]triazin-5-yl]carbonyl}-3-pyridinyl)-3-[2-(methyloxy)phenyl]urea | 446 | 3.19$^a$ |

HPLC and LC-MS analysis conditions:
$^a$Method A: Chromolith SpeedROD 4.6 x 50 mm, 5 μm column;

Example 83

1-(3-{[4-amino-7-(1-methylethyl)pyrrolo [2,1-f][1,2,4]triazin-5-yl]carbonyl}phenyl)-3-(3-cyclopropyl-1-methyl-1H-pyrazol-5-yl)urea

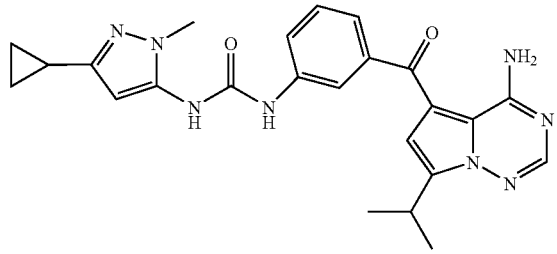

A solution of 1,1'-carbonyldiimidazole (21 mg, 0.13 mmol) in CH$_2$Cl$_2$ (1 mL) was treated with a solution of 3-cyclopropyl-1-methyl-1H-pyrazol-5-amine (16 g, 0.12 mmol) in CH$_2$Cl$_2$ (1 mL), dropwise over 15 minutes. The reaction was stirred at room temperature for one hour and 1H (35 mg, 0.12 mmol) was added in one portion. The reaction was stirred for 18 hours and then concentrated. The crude product was purified by preparative reversed-phase HPLC ((YMC ODS-A 20×100 mm, 10-90% aqueous methanol containing 0.1% TFA, 30 min gradient, monitored at 220 nm) and the fractions containing the desired product were lyophilized to dryness (15 mg, 28%). HPLC t$_R$=3.96 min (YMC S5 ODS 4.6×50 mm, 10-90% aqueous methanol containing 0.2% H$_3$PO$_4$, 4 min gradient, monitored at 220 nm). [M+H+]=459.24

Preparation of Amino-pyrazoles

A. Preparation of 2-(5-amino-3-tert-butyl-1H-pyrazol-1-yl)ethanol

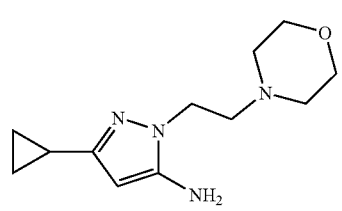

A solution of 4,4-dimethyl-3-oxopentanenitrile (125 mg, 1.0 mmol) and 2-hydroxyethyl hydrazine (75 mg, 1.0 mmol) in EtOH was heated to 100° C. for 18 hours. The reaction mixture was concentrated under reduced pressure and the crude product was purified by flash chromatography (SiO$_2$, 0% to 10% MeOH containing 1% NH$_4$OH/CH$_2$Cl$_2$) to afford the desired amino-pyrazole.

B. Preparation of 3-cyclopropyl-1-(2-morpholinoethyl)-1H-pyrazol-5-amine

A mixture of 3-cyclopropyl-1H-pyrazole-5-amine (250 mg, 2.0 mmol), 4-(2-chloroethyl)morpholine HCl salt (372 mg, 2.0 mmol) and potassium carbonate (829 mg, 6.0 mmol) in dry DMF (10 mL) was stirred at room temperature overnight. After being diluted with ethyl acetate (50 mL), the reaction mixture was filtered through a pad of Celite and rinsed with ethyl acetate (2×15 mL). The combined filtrates were concentrated in vacuo and purified by ISCO (CH$_2$Cl$_2$-MeOH—NH$_4$OH: 100:0:0 to 90:10:1) on silica gel to afford the desired amino-pyrazole.

Examples 84 to 92

Examples 84 to 92 were prepared from Compound 1H and the corresponding amino-pyrazoles utilizing procedure analogous to the one for Compound 83 described above. The final products were purified by trituration, or recrystallization, or preparative HPLC (C18 reverse-phase, YMC ODS S5, 5μm, 20×100 mm, using H2O-MeOH-0.1% TFA as eluents).

| Ex# | R | Name | [M + H]$^+$ | HPLC Ret Time (min) |
|---|---|---|---|---|
| 84 | (3-tert-butyl-1-phenyl-1H-pyrazol-5-yl) | 1-(3-{[4-amino-7-(1-methylethyl)pyrrolo[2,1-f][1,2,4]triazin-5-yl]carbonyl}phenyl)-3-[3-(1,1-dimethylethyl)-1-phenyl-1H-pyrazol-5-yl]urea | 537 | 3.685$^a$ |
| 85 | (3-tert-butyl-1-methyl-1H-pyrazol-5-yl) | 1-(3-{[4-amino-7-(1-methylethyl)pyrrolo[2,1-f][1,2,4]triazin-5-yl]carbonyl}phenyl)-3-[3-(1,1-dimethylethyl)-1-methyl-1H-pyrazol-5-yl]urea | 475 | 3.30$^a$ |
| 86 | (3-tert-butyl-1-(2-hydroxyethyl)-1H-pyrazol-5-yl) | 1-(3-{[4-amino-7-(1-methylethyl)pyrrolo[2,1-f][1,2,4]triazin-5-yl]carbonyl}phenyl)-3-[3-(1,1-dimethylethyl)-1-(2-hydroxyethyl)-1H-pyrazol-5-yl]urea | 505 | 3.27$^a$ |
| 87 | (3-cyclopropyl-1H-pyrazol-5-yl) | 1-(3-{[4-amino-7-(1-methylethyl)pyrrolo[2,1-f][1,2,4]triazin-5-yl]carbonyl}phenyl)-3-(3-cyclopropyl-1H-pyrazol-5-yl)urea | 445 | 3.44 |

-continued

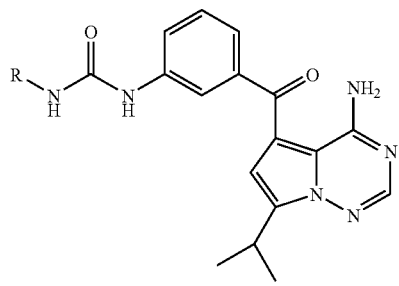

| Ex# | R | Name | [M + H]+ | HPLC Ret Time (min) |
|---|---|---|---|---|
| 88 | (1H-1,2,4-triazol-3-yl) | 1-(3-{[4-amino-7-(1-methylethyl)pyrrolo[2,1-f][1,2,4]triazin-5-yl]carbonyl}phenyl)-3-(1H-1,2,4-triazol-3-yl)urea | 406 | |
| 89 | (3-cyclopropyl-1-[2-(4-morpholinyl)ethyl]-1H-pyrazol-5-yl) | 1-(3-{[4-amino-7-(1-methylethyl)pyrrolo[2,1-f][1,2,4]triazin-5-yl]carbonyl}phenyl)-3-{3-cyclopropyl-1-[2-(4-morpholinyl)ethyl]-1H-pyrazol-5-yl}urea | 558 | 2.89[a] |
| 90 | (1-methyl-1H-pyrazol-5-yl) | 1-(3-{[4-amino-7-(1-methylethyl)pyrrolo[2,1-f][1,2,4]triazin-5-yl]carbonyl}phenyl)-3-(1-methyl-1H-pyrazol-5-yl)urea | 419 | |
| 91 | (1-ethyl-1H-pyrazol-5-yl) | 1-(3-{[4-amino-7-(1-methylethyl)pyrrolo[2,1-f][1,2,4]triazin-5-yl]carbonyl}phenyl)-3-(1-ethyl-1H-pyrazol-5-yl)urea | 433 | |
| 92 | (5-cyclopropyl-1H-1,2,4-triazol-3-yl) | 1-(3-{[4-amino-7-(1-methylethyl)pyrrolo[2,1-f][1,2,4]triazin-5-yl]carbonyl}phenyl)-3-(5-cyclopropyl-1H-1,2,4-triazol-3-yl)urea | 446 | |

HPLC and LC-MS analysis conditions:
[a]Method A: Chromolith SpeedROD 4.6 x 50 mm, 5 μm column;

Examples 93 to 94

Examples 93 and 94 were prepared from Compound 68B and the corresponding amino-pyrazoles utilizing procedure analogous to the one for Compound 83 described above. The final products were purified by trituration, or recrystallization, or preparative HPLC (C18 reverse-phase, YMC ODS S5, 5μm, 20×100 mm, using H2O-MeOH-0.1% TFA as eluents).

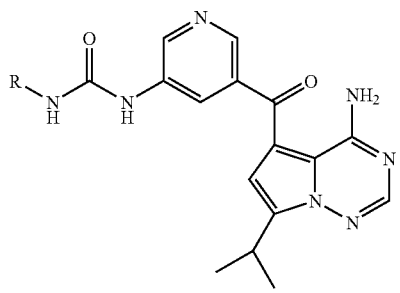

| Ex# | R | Name | [M + H]+ | HPLC Ret Time (min) |
|---|---|---|---|---|
| 93 | (1-methyl-3-isopropyl-1H-pyrazol-5-yl) | 1-(5-{[4-amino-7-(1-methylethyl)pyrrolo[2,1-f][1,2,4]triazin-5-yl]carbonyl}-3-pyridinyl)-3-[1-methyl-3-(1-methylethyl)-1H-pyrazol-5-yl]urea | 462 | 2.92$^a$ |
| 94 | (1-methyl-3-cyclopropyl-1H-pyrazol-5-yl) | 1-(5-{[4-amino-7-(1-methylethyl)pyrrolo[2,1-f][1,2,4]triazin-5-yl]carbonyl}-3-pyridinyl)-3-(3-cyclopropyl-1-methyl-1H-pyrazol-5-yl)urea | 460 | 2.80$^a$ |

HPLC and LC-MS analysis conditions:
$^a$Method A: Chromolith SpeedROD 4.6 x 50 mm, 5 μm column;

Example 95

1-[3-({4-amino-7-[3-(1-piperidinyl)-1-propyn-1-yl]pyrrolo[2,1-f][1,2,4]triazin-5-yl}carbonyl)phenyl]-3-(2,4-dichlorophenyl)urea

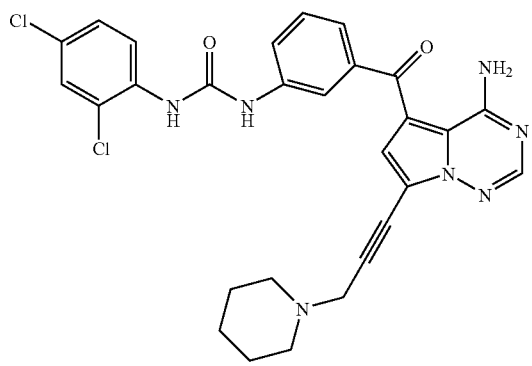

95A. Preparation of Ethyl 7-bromo-4-hydroxypyrrolo[1,2-f][1,2,4]triazine-5-carboxylate

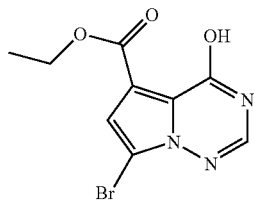

A suspension of ethyl 4-hydroxypyrrolo[1,2-f][1,2,4]triazine-5-carboxylate (1.08 g, 5.23 mmol) and N-bromosuccinimide (0.90 g, 5.49 mmol) in CH$_2$Cl$_2$ was treated with trifluoroacetic acid (1 mL) at room temperature. The reaction mixture was stirred for five hours and then concentrated to dryness. The residue was treated with EtOAc (10 mL) and again concentrated to dryness. The resulting solid was collected by vacuum filtration and washed with EtOAc to afford the title compound (1.3 g, 87%). Compound 95A had an analytical HPLC retention time=2.203 min. (Chromolith SpeedROD column 4.6×50 mm, 10-90% aqueous methanol over 4 minutes containing 0.1% TFA, 4 ml/min, monitoring at 220 nm) and a LC/MS M+-1=286+.

95B. Preparation of 7-bromo-4-hydroxypyrrolo[1,2-f][1,2,4]triazine-5-carboxylic acid

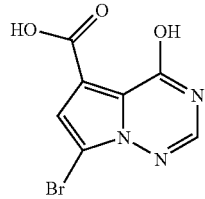

A solution of 95A (1.1 g, 3.85 mmol) in THF (10 mL) and MeOH (10 mL) was treated with a solution of LiOH hydrate (0.5 g, 11.6 mmol) in water (5 mL). The reaction was stirred at room temperature for 3.5 hours and then heated to 50° C. for one hour. The reaction mixture was concentrated to remove the THF and MeOH and the residue was diluted with water. The reaction mixture was made acidic with 2 N HCl and the white solid precipitate was collected by filtration and dried under vacuum (1.02 g, 100%). Compound 95B had an analytical HPLC retention time=1.408 min. (Chromolith SpeedROD column 4.6×50 mm, 10-90% aqueous methanol over 4 minutes containing 0.1% TFA, 4 ml/min, monitoring at 220 nm) and a LC/MS M+-1=258+.

95C. Preparation of 7-bromo-4-chloro-N-methoxy-N-methylpyrrolo[1,2-f][1,2,4]triazine-5-carboxamide

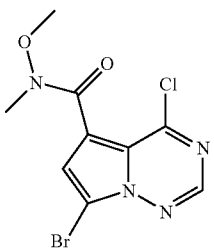

A suspension of 95B (1.0 g, 3.88 mmol) in SOCl₂ (20 mL) was treated with DMF (5 drops) and heated at 80° C. for three hours. The reaction mixture was concentrated to dryness and dissolved in CH₂Cl₂ and concentrated to dryness. The resulting solid was dried under high vacuum for 24 hours, and then dissolved in CH₂Cl₂ (20 ml). The mixture was treated with N,O-dimethyl hydroxylamine hydrochloride (340 mg, 3.49 mmol) and cooled to 0° C. Triethylamine (1.61 mL, 11.5 mmol) was added and the reaction mixture was stirred at 0° C. for one hour. The solution was diluted with CH₂Cl₂ and washed with cold 10% citric acid, followed by saturated aqueous NaHCO₃ and brine. The organic layer was dried (Na₂SO4), filtered and concentrated to dryness. The crude chloride was purified by flash chromatography (SiO₂, 0% to 100% EtOAc/Hexanes) to afford the title compound as a solid (0.99 g, 83%). HPLC $t_R$=1.707 min (Chromolith SpeedROD column 4.6×50 mm, 10-90% aqueous methanol over 4 minutes containing 0.1% TFA, 4 ml/min, monitoring at 220 nm). [M+H+]=319.

95D. Preparation of 4-amino-7-bromo-N-methoxy-N-methylpyrrolo[1,2-f][1,2,4]triazine-5-carboxamide

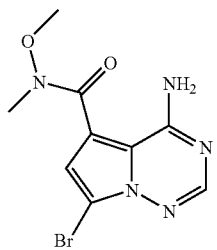

A solution of 95C (0.97 g, 3.0 mmol) in 1,4-dioxane (10 mL) was treated with NH₄OH (10 mL) and stirred at room temperature for 20 minutes. The solvent was removed under reduced pressure and the solid residue was treated with water and filtered. The resulting solid was dried under vacuum to afford the title compound (0.83 g, 93%). Compound 95D had an analytical HPLC retention time=1.725 min. (Chromolith SpeedROD column 4.6×50 mm, 10-90% aqueous methanol over 4 minutes containing 0.1% TFA, 4 ml/min, monitoring at 220 nm) and a LC/MS M+-1=300+.

95E. Preparation of (4-amino-7-bromopyrrolo[1,2-f][1,2,4]triazin-5-yl)(3-[bis(trimethylsilyl)-amino]phenyl)methanone

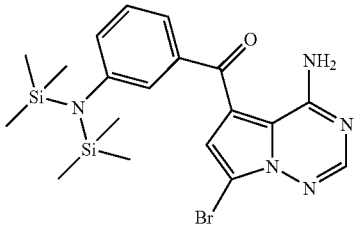

A solution of 95D (250 mg, 0.67 mmol) in THF (10 mL) at 0° C. was added 3-[bis(trimethylsilyl)amino]phenylmagnesium chloride (1.0 M in THF, 6.7 mL, 6.7 mmol) via addition funnel over 20 minutes. The solution was stirred for one hour at 0° C. and additional 3-[bis(trimethylsilyl)amino]phenylmagnesium chloride (1.0 M in THF, 1.2 mL) was added. After one hour, the reaction was quenched with saturated aqueous NH₄Cl (10 mL). The layers were separated and the aqueous layer was extracted with EtOAc (3×10 mL). The combined organic layers were dried (Na₂SO₄), filtered, and one half of the solvent was removed under reduced pressure. The resulting suspension was cooled to 0° C. and diluted with hexanes (20 mL). The solid was collected by filtration and washed with hexanes to afford the desired compound (200 mg, 64%). ¹H NMR (400 MHz, DMSO-d₆) d 9.07 (s, 1H), 8.54 (s, 1H), 8.15 (s, 1H), 7.39 (m, 2H), 7.12 (m, 2H), 6.87 (s, 1H), 0.004 (s, 18H).

95F. Preparation of (4-amino-7-bromopyrrolo[1,2-f][1,2,4]triazin-5-yl)(3-aminophenyl)methanone

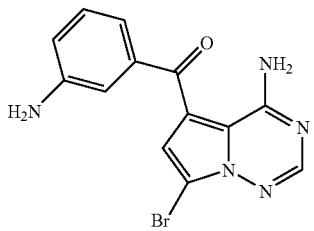

A solution of 95E (640 mg, 1.35 mmol) in CH₃OH (30 mL) was treated with trifluoroacetic acid (1.5 mL) at room temperature and stirred for two hours. The resulting solution was concentrated and dried under vacuum to afford 95F (445 mg, 100%). HPLC $t_R$=1.95 min (YMC S5 Combiscreen 4.6×50 mm, 10-90% aqueous methanol containing 0.2% $H_3PO_4$, 4 min gradient, monitored at 220 nm). [M+H+]=332.14.

95G. Preparation of 1-{3-[(4-amino-7-bromopyrrolo[2,1-f][1,2,4]triazin-5-yl)carbonyl]phenyl}-3-(2,4-dichlorophenyl)urea

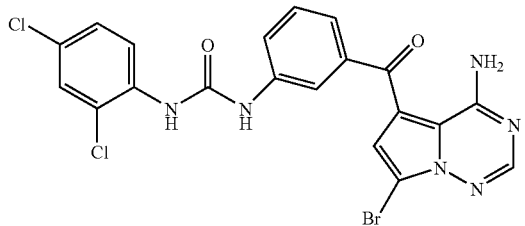

A solution of 95E (100 mg, 0.21 mmol) in $CH_2Cl_2$ (5 mL) was treated with trifluoroacetic acid (1 mL) at room temperature and was stirred for two hours. The reaction mixture was concentrated, dissolved in toluene and concentrated again. The resulting residue was dissolved in acetonitrile (2 mL) and treated with 2,4-dichloroisocyanate (39 mg, 0.23 mmol). The reaction was stirred at room temperature for 18 hours, and then filtered. The solid product was washed with cold acetonitrile and dried under vacuum to afford 95G (85 mg, 79%). Compound 95G had an analytical HPLC retention time=3.878 min. (Chromolith SpeedROD column 4.6×50 mm, 10-90% aqueous methanol over 4 minutes containing 0.1% TFA, 4 ml/min, monitoring at 220 nm) and a LC/MS M⁺+1=518.8⁺.

95H. Preparation of 1-[3-({4-amino-7-[3-(1-piperidinyl)-1-propyn-1-yl]pyrrolo[2,1-f][1,2,4]triazin-5-yl}carbonyl)phenyl]-3-(2,4-dichlorophenyl)urea

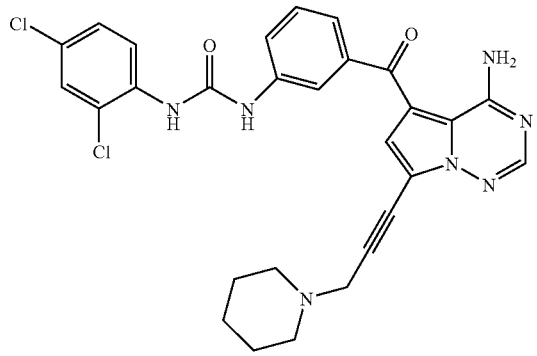

A solution of piperidine (2 mL) and propargyl bromide (80 wt % in toluene, 0.02 mL, 0.19 mmol) was purged with argon for 10 minutes. The solution was treated with 95G (20 mg, 0.04 mmol), CuI (1 mg, 0.008 mmol) and PdCl₂(PPh₃)₂ (3 mg, 0.004 mmol). The reaction mixture was heated to 80° C. for one hour and then concentrated. The residue was purified by flash chromatography (SiO₂, 0% to 10% MeOH/CH₂Cl₂) to afford the desired compound (13 mg, 62%). HPLC $t_R$=3.17 min (Chromolith SpeedROD 4.6×50 mm, 10-90% aqueous methanol containing 0.1% TFA, 4 min gradient, monitored at 254 nm). [M+H+]=562.27.

Example 96

1-[3-({4-amino-7-[3-(4-morpholinyl)-1-propyn-1-yl]pyrrolo[2,1-f][1,2,4]triazin-5-yl}carbonyl)phenyl]-3-(2,4-dichlorophenyl)urea

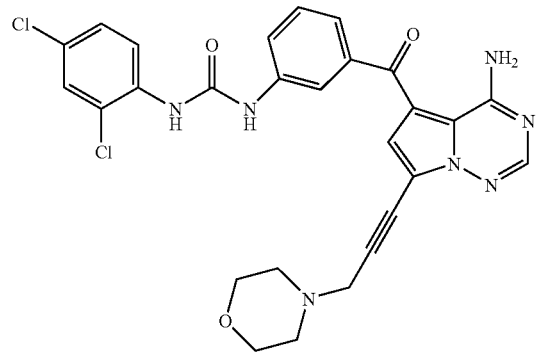

Example 96 was prepared in a manner analogous to Example 95 using morpholine in the place of piperidine. HPLC $t_R$=3.07 min (Chromolith SpeedROD 4.6×50 mm, 10-90% aqueous methanol containing 0.1% TFA, 4 min gradient, monitored at 254 nm). [M+H+]=564.22.

Example 97

1-[5-({4-amino-7-[3-(dimethylamino)-1-propyn-1-yl]pyrrolo[2,1-f][1,2,4]triazin-5-yl}carbonyl)-3-pyridinyl]-3-(2,4-dichlorophenyl)urea

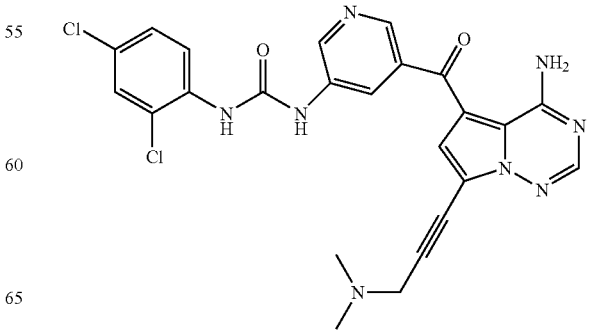

97A. Preparation of 4-amino-7-(3-(dimethylamino) prop-1-ynyl)-N-methoxy-N-methylpyrrolo[1,2-f][1,2,4]triazine-5-carboxamide

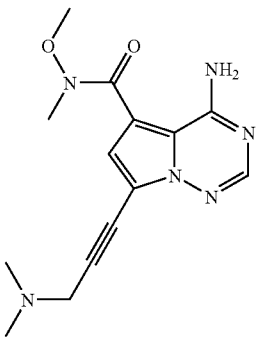

A solution of triethylamine (6 mL) and DMF (3 mL) was purged with argon for 30 minutes and treated with 95D (300 mg, 1.0 mmol). N,N-dimethylprop-2-yn-1-amine (0.5 mL, 5.0 mmol), CuI (38 mg, 0.2 mmol) and $PdCl_2(PPh_3)_2$ (70 mg, 0.1 mmol) were added. The reaction mixture was warmed to 60° C. for three hours and then cooled to room temperature and concentrated to dryness. The crude product was purified by flash chromatography ($SiO_2$, 0% to 10% $MeOH/CH_2Cl_2$) to afford 97A as a solid (335 mg, 100%). HPLC tR=1.08 min (YMC S5 Combiscreen ODS 4.6×50 mm, 10-90% aqueous methanol containing 0.2% $H_3PO_4$, 4 min gradient, monitored at 220 nm).

97B. Preparation of Tert-butyl 3-(4-amino-7-(3-(dimethylamino)prop-1-ynyl)pyrrolo[1,2-f][1,2,4]triazine-5-carbonyl)phenylcarbamate

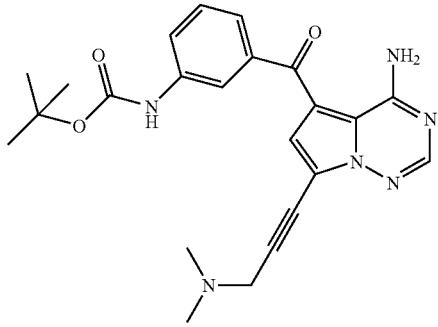

A solution of 97A (900 mg, 3.3 mmol) in THF (15 mL) was cooled to −15° C. and $Bu_2Mg$ (1.0 M in hexanes, 1.65 mL, 1.65 mmol) was added dropwise over 20 minutes. The resulting solution was stirred at −15° C. for one hour and then cooled to −78° C. A solution of nBuLi (1.6 M in heptane, 2.0 mL, 3.3 mmol) was added and the resulting suspension was warmed to 0° C. for thirty minutes. To this suspension was added 97B (335 mg, 1.1 mmol) in one portion and the reaction was warmed to room temperature for 18 hours. The reaction mixture was then poured into saturated aqueous $NaHCO_3$ (30 mL) and the layers were separated. The aqueous layer was extracted with EtOAc (3×25 mL) and the combined organic layers were dried ($Na_2SO_4$), filtered and concentrated to dryness. The crude product was purified by flash chromatography ($SiO_2$, 0% to 10% $MeOH/CH_2Cl_2$) to afford the title compound (105 mg, 22%). HPLC $t_R$=2.43 min (Chromolith SpeedROD 4.6×50 mm, 10-90% aqueous methanol containing 0.1% TFA, 4 min gradient, monitored at 220 nm). $[M+H]^+$=436.3.

97C. Preparation of (4-amino-7-(3-(dimethylamino) prop-1-ynyl)pyrrolo[1,2-f][1,2,4]triazin-5-yl)(3-aminophenyl)methanone

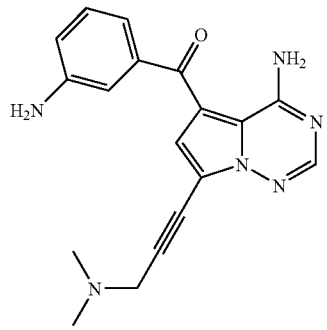

A solution of 97B (105 mg, 0.24 mmol) in $CH_2Cl_2$ (10 mL) was treated with trifluoroacetic acid (1 mL) at 0° C. The reaction mixture was stirred at room temperature for three hours and then concentrated to a film and used in the next step without further purification.

97D. Preparation of 1-[5-({4-amino-7-[3-(dimethylamino)-1-propyn-1-yl]pyrrolo[2,1-f][1,2,4]triazin-5-yl}carbonyl)-3-pyridinyl]-3-(2,4-dichlorophenyl) urea

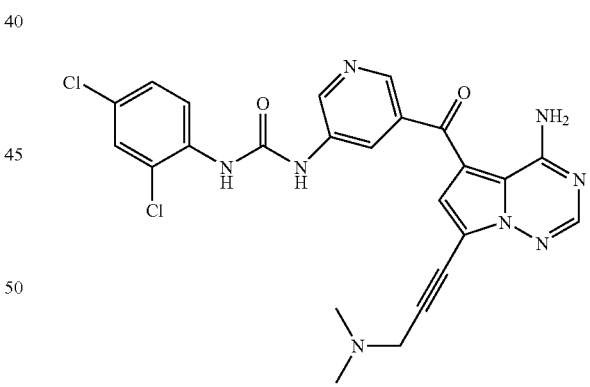

A solution of 97C (0.12 mmol) in pyridine (3 mL) was treated with 2,4-dichloroisocyanate (25 mg, 0.13 mmol) at room temperature and stirred for three hours. The reaction mixture was then concentrated to dryness and the crude product was purified by preparative reversed-phase HPLC (YMC ODS-A 20×100 mm, 10%-90% aqueous methanol containing 0.1% TFA, 20 min gradient, monitored at 220 nm) to afford the desired compound (33 mg). HPLC $t_R$=2.91 (YMC S5 Combiscreen ODS 4.6×50 mm, 10-90% aqueous methanol containing 0.2% $H_3PO_4$, 4 min gradient, monitored at 254 nm) [M+H+]=523.14.

Example 98

1-[5-({4-amino-7-[3-(dimethylamino)-1-propyn-1-yl]pyrrolo[2,1-f][1,2,4]triazin-5-yl}carbonyl)-3-pyridinyl]-3-[2-(methyloxy)phenyl]urea

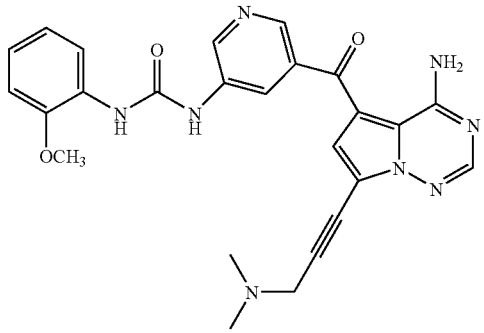

Example 98 was prepared from 97C and 2-methoxyisocyante in a manner analogous to Example 97. HPLC $t_R$=2.43 (YMC S5 Combiscreen ODS 4.6×50 mm, 10-90% aqueous methanol containing 0.2% $H_3PO_4$, 4 min gradient, monitored at 254 nm) [M+H+]=485.24.

Example 99

1-{3-[(4-aminopyrrolo[2,1-f][1,2,4]triazin-5-yl)carbonyl]phenyl}-3-(3-cyclopropyl-1-methyl-1H-pyrazol-5-yl)urea

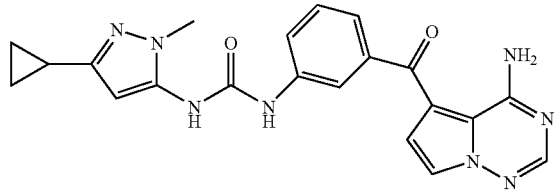

99A. Preparation of 1-{3-[(4-amino-7-bromopyrrolo[2,1-f][1,2,4]triazin-5-yl)carbonyl]phenyl}-3-(3-cyclopropyl-1-methyl-1H-pyrazol-5-yl)urea

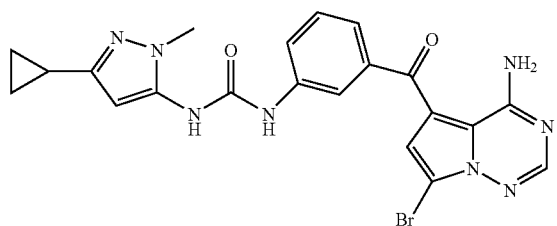

A solution of 1,1'-carbonyldiimidazole (27 mg, 0.17 mmol) and 3-cyclopropyl-1-methyl-1H-pyrazol-5-amine (21 mg, 0.15 mmol) in $CH_2Cl_2$ (1 mL) was stirred at room temperature for three hours. The reaction mixture was then treated with 95F (50 mg, 0.15 mmol) in one portion and stirred at room temperature for 90 minutes. The resulting suspension was diluted with EtOAc and water and filtered. The solid was collected by filtration to afford the title compound (7.7 mg). Compound 99A had an analytical HPLC retention time=2.986 min. (Chromolith SpeedROD column 4.6×50 mm, 10-90% aqueous methanol over 4 minutes containing 0.1% TFA, 4 ml/min, monitoring at 220 nm) and a LC/MS $M^++1$=495$^+$. The EtOAc layer was concentrated and used directly in the next step.

99B. Preparation of 1-{3-[(4-aminopyrrolo[2,1-f][1,2,4]triazin-5-yl)carbonyl]phenyl}-3-(3-cyclopropyl-1-methyl-1H-pyrazol-5-yl)urea

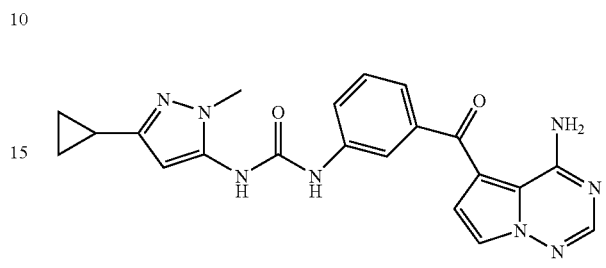

The above crude 99A was dissolved in EtOAc (20 mL) and MeOH (20 mL) and treated with 10% Pd/C. The reaction mixture was stirred under a hydrogen atmosphere for 4.5 hours and then filtered to remove the catalyst. The filtrate was concentrated and the resulting solid was collected by filtration, rinsed with EtOAc and dried to give the desired product (23 mg). Compound 99B had an analytical HPLC retention time=2.433 min. (Chromolith SpeedROD column 4.6×50 mm, 10%-90% aqueous methanol over 4 minutes containing 0.1% TFA, 4 ml/min, monitoring at 220 nm) and a LC/MS $M^++1$=417$^+$.

Example 100

1-[3-({4-amino-7-[3-(dimethylamino)-1-propyn-1-yl]pyrrolo[2,1-f][1,2,4]triazin-5-yl}carbonyl)phenyl]-3-(3-cyclopropyl-1-methyl-1H-pyrazol-5-yl)urea

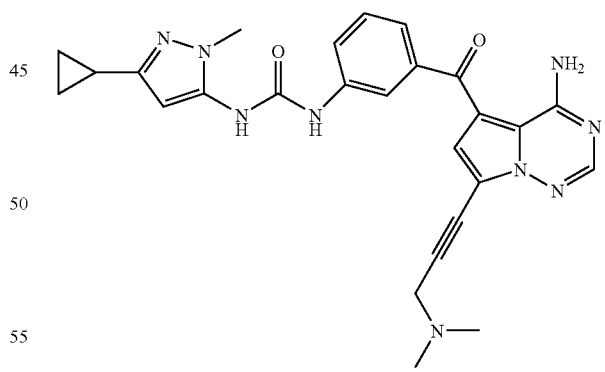

Example 100 was prepared from 97C (23 mg, 0.07 mmol) and 3-cyclopropyl-1-methyl-1H-pyrazol-5-amine (13 mg, 0.097 mmol) in a manner analogous to Example 99. The solution was purified by flash chromatography ($SiO_2$, 0% to 10% MeOH/$CH_2Cl_2$) to afford desired compound (9.3 mg). Compound 100 had an analytical HPLC retention time=2.220 min. (Chromolith SpeedROD column 4.6×50 mm, 10-90% aqueous methanol over 4 minutes containing 0.1% TFA, 4 ml/min, monitoring at 220 nm) and a LC/MS $M^++1$=498$^+$.

Example 101

1-{3-[(4-amino-7-methylpyrrolo[2,1-f][1,2,4]triazin-5-yl)carbonyl]phenyl}-3-(3-cyclopropyl-1-methyl-1H-pyrazol-5-yl)urea

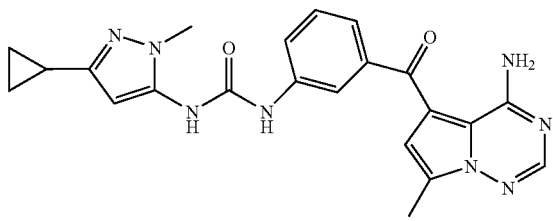

101A. Preparation of (4-amino-7-methylpyrrolo[1,2-f][1,2,4]triazin-5-yl)(3-aminophenyl)methanone

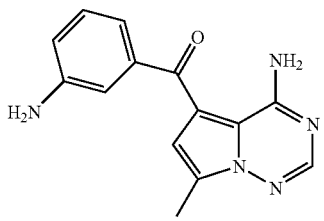

A solution of 95F (50 mg, 0.15 mmol) in DMF (0.5 mL) was treated with tetramethyltin (81 mg, 0.45 mmol) and PdCl$_2$(PPh$_3$)$_2$ (10 mg, 0.015 mmol). The reaction mixture was stirred at 80° C. for two hours. Additional PdCl$_2$(PPh$_3$)$_2$ (10 mg, 0.015 mmol) was added and the reaction was heated for 18 hours at 110° C. The reaction was cooled to room temperature and diluted with water and EtOAc. The solid material was removed by filtration and the filtrate was washed with 10% aqueous LiCl. The organic layer was concentrated and the crude product was purified by reversed phase preparative HPLC (YMC S5 ODS 20×100 mm, 10-90% aqueous methanol over 10 minutes containing 0.1% TFA, 20 ml/min, monitoring at 220 nm) to afford the desired compound as TFA salt (6 mg). Compound 101A had an analytical HPLC retention time=1.293 min. (Chromolith SpeedROD column 4.6×50 mm, 10-90% aqueous methanol over 4 minutes containing 0.1% TFA, 4 ml/min, monitoring at 220 nm) and a LC/MS $M^++1=268^+$.

101B. Preparation of 1-{3-[(4-amino-7-methylpyrrolo[2,1-f][1,2,4]triazin-5-yl)carbonyl]phenyl}-3-(3-cyclopropyl-1-methyl-1H-pyrazol-5-yl)urea

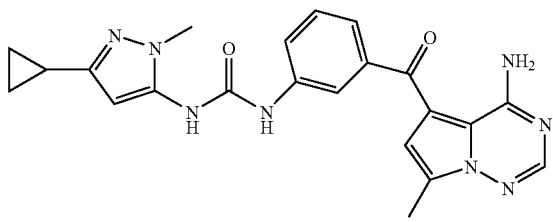

A solution of 3-cyclopropyl-1-methyl-1H-pyrazol-5-amine (12 mg, 0.09 mmol) and 1,1'-carbonylimidazole (14 mg, 0.09 mmol) in CH$_2$Cl$_2$ (0.5 mL) was stirred at room temperature for 18 hours. The solution was added to a solution of 101A (6.0 mg, 0.016 mmol) and triethylamine (2 drops) in CH$_2$Cl$_2$ (0.5 mL). The resulting mixture was stirred for two hours and then concentrated. The crude product was purified by preparative reversed phase HPLC (YMC S5 ODS 20×100 mm, 10-90% aqueous methanol over 10 minutes containing 0.1% TFA, 20 ml/min, monitoring at 220 nm) to afford the title compound (5.6 mg). Compound 101B had an analytical HPLC retention time=2.600 min. (Chromolith SpeedROD column 4.6×50 mm, 10-90% aqueous methanol over 4 minutes containing 0.1% TFA, 4 ml/min, monitoring at 220 nm) and a LC/MS $M^++1=431^+$.

Example 102

1-(3-{[4-amino-7-(4-piperidinyl)pyrrolo[2,1-f][1,2,4]triazin-5-yl]carbonyl}phenyl)-3-(2,4-dichlorophenyl)urea

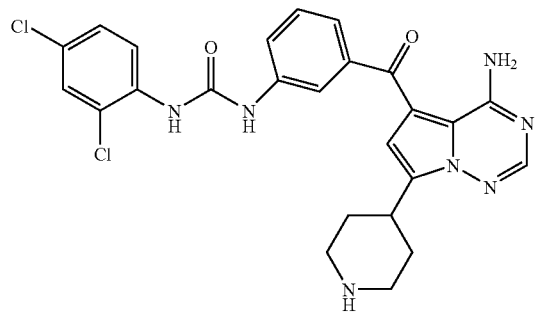

A mixture of Zn dust (42 mg) in dimethylacetamide (0.5 mL) was treated with a mixture of chlorotrimethylsilane/1,2-dibromoethane (7/5 v/v, 0.020 mL). The reaction was heated to 50° C. for 30 minutes and then slowly cooled to room temperature. A solution of tert-butyl 4-iodopiperidine-1-carboxylate (165 mg, 0.53 mmol) in dimethylacetamide (1 mL) was added. The reaction was stirred at room temperature for one hour. This solution was added to a mixture of 95G (22 mg), PdCl$_2$(dppf)$_2$ (3 mg), CuI (6 mg) in dimethylactamide (1.2 mL). The reaction was heated under a nitrogen atmosphere at 80° C. for 18 hours. The reaction was diluted with water and extracted with EtOAc. The resulting solid was collected by filtration and the layers were separated. The organic layer was combined with the solid material and concentrated to dryness. The resulting residue was dissolved in CH$_2$Cl$_2$ (1 mL) and treated with trifluoroacetic acid (2 mL). The reaction mixture was concentrated and the residue was purified by preparative reversed phase HPLC (YMC S5 ODS 20×100 mm, 10-90% aqueous methanol over 10 minutes containing 0.1% TFA, 20 ml/min, monitoring at 220 nm). The desired fractions were passed through an SCX cartridge and concentrated to afford the desired compound (1.8 mg). Compound 102 had an analytical HPLC retention time=2.900 min. (Chromolith SpeedROD column 4.6×50 mm, 10-90% aqueous methanol over 4 minutes containing 0.1% TFA, 4 ml/min, monitoring at 220 nm) and a LC/MS $M^++1=524^+$.

Example 103

(2S)-2-amino-3-(4-amino-5-{[3-({[(2,4-dichlorophenyl)amino]carbonyl}amino)phenyl]carbonyl}pyrrolo[2,1-f][1,2,4]triazin-7-yl)propanoic acid

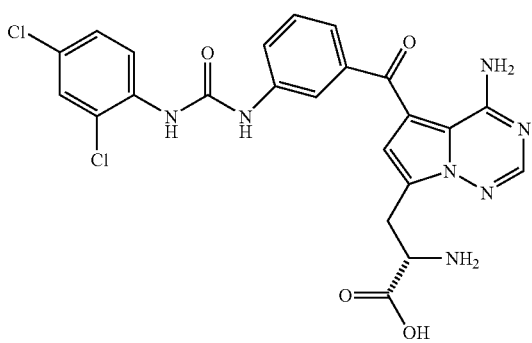

A mixture of zinc dust (300 mg) in dimethylacetamide (DMA) (0.3 mL) at 50° C. was treated with a solution of chlorotrimethylsilane/1,2-dibromoethane (7/5 v/v, 0.04 mL) and the reaction was stirred at room temperature for 30 minutes. A solution of methyl 2-(tert-butoxycarbonylamino)-3-iodopropanoate (247 mg, 0.75 mmol) in DMA (1 mL) was slowly added and the reaction was stirred for 40 minutes. This mixture was added to a mixture of 95G (35 mg), PdCl$_2$(dppf)$_2$ (7 mg), and CuI (10 mg) in DMA (0.8 mL). The reaction was heated to 80° C. for 18 hours. Water was added and the solid precipitate was collected by filtration. The solid was treated with 33% HBr/AcOH and then concentrate. The residue was dissolved in THF/MeOH and water and treated with LiOH and stirred at room temperature for two hours. The reaction mixture was neutralized with trifluoroacetic acid and purified by preparative reversed phase HPLC to afford the desired product (1.7 mg). Compound 103 had an analytical HPLC retention time=2.906 min. (Chromolith SpeedROD column 4.6×50 mm, 10-90% aqueous methanol over 4 minutes containing 0.1% TFA, 4 ml/min, monitoring at 220 nm) and a LC/MS M$^+$+1=528$^+$.

Example 104

1-(3-{1-[4-amino-7-(1-methylethyl)pyrrolo[2,1-f][1,2,4]triazin-5-yl]-1-hydroxyethyl}phenyl)-3-(2,4-dichlorophenyl)urea

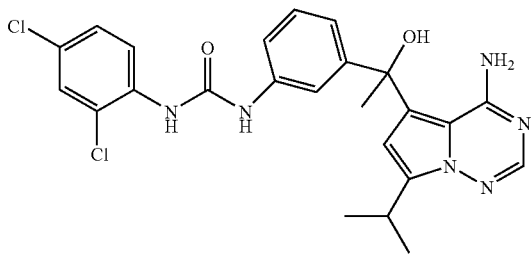

A solution of Compound 1 (23 mg, 0.048 mmol) in THF (2.5 mL) at 0° C. was treated with CH$_3$MgBr (3.0 M in Et$_2$O, 0.1 mL, 0.3 mmol). The reaction was stirred for three hours and additional CH$_3$MgBr (3.0 M in Et$_2$O, 0.2 mL, 0.6 mmol) was added. The solution was stirred for an additional 30 minutes and more CH$_3$MgBr (3.0 M in Et$_2$O, 0.5 mL) was added. The reaction mixture was quenched with saturated aqueous NH$_4$Cl, diluted with water and extracted with EtOAc. The combined extracts were concentrated and purified by preparative reversed phase HPLC (YMC S5 ODS 20×100 mm, 10-90% aqueous methanol over 10 minutes containing 0.1% TFA, 20 ml/min, monitoring at 220 nm). The fractions containing the desired compound were concentrated and the free base was obtained using saturated aqueous NaHCO$_3$ to afford the desired compound (12.6 mg). Compound 104 had an analytical HPLC retention time=3.415 min. (Chromolith SpeedROD column 4.6×50 mm, 10-90% aqueous methanol over 4 minutes containing 0.1% TFA, 4 ml/min, monitoring at 220 nm) and a LC/MS M$^+$+1=499$^+$.

Example 105

1-{3-[(4-amino-7-ethylpyrrolo[2,1-f][1,2,4]triazin-5-yl)carbonyl]phenyl}-3-(2,4-dichlorophenyl)urea

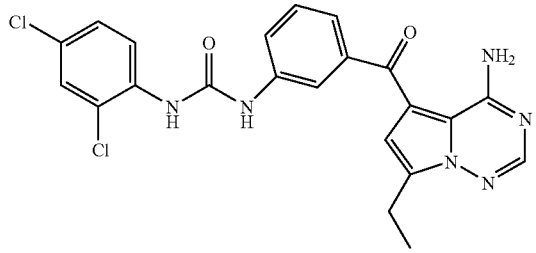

105A Preparation of 4-amino-N-methoxy-N-methyl-7-((trimethylsilyl)ethynyl)pyrrolo[1,2-f][1,2,4]triazine-5-carboxamide

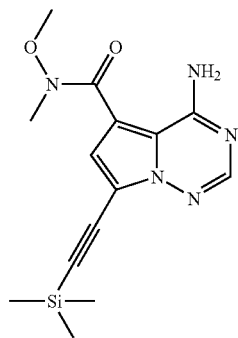

A solution of 95D (50 mg, 0.16 mmol) in DMA (2 mL) was purged with argon and treated with PdCl$_2$(dppf)$_2$—CH$_2$Cl$_2$ complex (13 mg, 0.017 mmol), CuI (6 mg, 0.032 mmol) and ethynyltrimethylsilane (0.45 mL, 3.2 mmol). The reaction mixture was warmed to 50° C. and stirred for seven hours. The mixture was then poured into EtOAc (10 mL) and washed with saturated aqueous LiCl solution (3×10 mL). The organic layer was dried (Na$_2$SO$_4$), filtered and concentrate. The crude product was purified by flash chromatography (SiO$_2$, 0% to 2% MeOH/CH$_2$Cl$_2$) to afford the desired compound (12 mg, 24%). HPLC tR=3.34 min (YMC S5 Combiscreen ODS 4.6×50 mm, 10-90% aqueous methanol containing 0.2% H$_3$PO$_4$, 4 min gradient, monitored at 220). [M+H]$^+$=318.24.

105B. Preparation of (4-amino-7-((trimethylsilyl)ethynyl)pyrrolo[1,2-f][1,2,4]triazin-5-yl)(3-(bis-trimethylsilylamino)phenyl)methanone

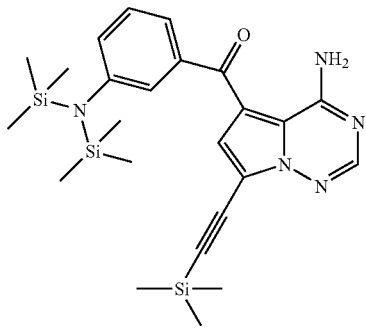

A solution of 105A (12 mg, 0.038 mmol) in THF (5 mL) was cooled to 0° C. and a solution of 3-[bis(trimethylsilyl)amino]phenylmagnesium chloride (1.0 M in THF, 0.38 mL, 0.38 mmol) was added. The reaction mixture was stirred at 0° C. for one hour and more 3-[bis(trimethylsilyl)amino]phenylmagnesium chloride (1.0 M in THF, 0.38 mL, 0.38 mmol) was added. The reaction mixture was stirred for one hour at 0° C. and warmed to room temperature. The reaction was quenched with saturated aqueous NH$_4$Cl (3 mL) and the layers were separated. The aqueous layer was extracted with EtOAc (3×10 mL) and the combined organic layers were dried (Na$_2$SO$_4$), filtered and concentrated to dryness. The crude product was purified by flash chromatography (SiO$_2$, 0% to 40% EtOAc/Hexanes) to afford the desired product (12 mg, 63%). HPLC tR=3.12 min (Phenomenex 5 u C18 4.6×50 mm column 10-90% aqueous methanol containing 0.1% TFA, 4min grad. monitored at 220 nm). [M+H]+=350.24.

105C. Preparation of (4-amino-7-ethynylpyrrolo[1,2-f][1,2,4]triazin-5-yl)(3-aminophenyl)methanone

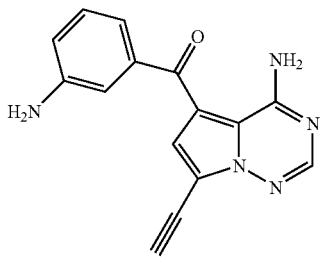

A solution of 105B (12 mg, 0.024 mmol) in MeOH (1 mL) at 0° C. was treated with 5% KOH in MeOH (1 mL). The reaction mixture was slowly warmed to room temperature and stirred for one hour. The reaction mixture was diluted with EtOAc (10 mL) and washed with water (10 mL). The organic layer was dried (Na$_2$SO$_4$), filtered and concentrated. The crude product was purified by flash chromatography (SiO$_2$, 0% to 2% MeOH/CH$_2$Cl$_2$) to afford the desired compound (4 mg, 60%). HPLC tR=1.81 min (YMC S5 Combiscreen ODS 4.6×50 mm, 10-90% aqueous methanol containing 0.2% H$_3$PO$_4$, 4 min gradient, monitored at 220). [M+H]+=278.32.

105D. Preparation of (4-amino-7-ethylpyrrolo[1,2-f][1,2,4]triazin-5-yl)(3-aminophenyl)methanone

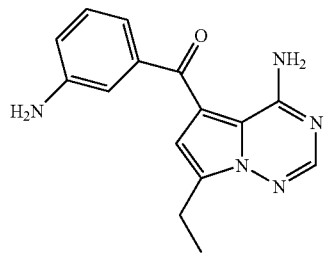

A solution of 105C (4 mg, 0.014 mmol) in MeOH (1 mL) was treated with 2,6-lutidine (0.015 mL) and Lindlar's catalyst (1 mg). The reaction mixture was stirred at room temperature under a hydrogen atmosphere for two hours and the filtered to remove catalyst. The filtrate was concentrated under reduced pressure and dried under vacuum to afford the title compound (4mg). HPLC tR=1.77 min (YMC S5 Combiscreen ODS 4.6×50 mm, 10-90% aqueous methanol containing 0.2% H$_3$PO$_4$, 4 min gradient, monitored at 220). [M+H]+=282.35.

105E. Preparation of 1-{3-[(4-amino-7-ethylpyrrolo[2,1-f][1,2,4]triazin-5-yl)carbonyl]phenyl}-3-(2,4-dichlorophenyl)urea

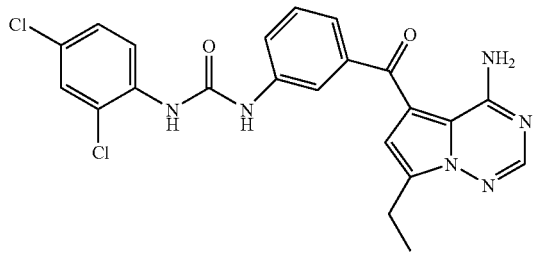

A solution of 105D (4 mg, 0.014 mmol) in acetonitrile (2 mL) was treated with 2,4-dichloroisocyante (2.6 mg, 0.014 mmol). The reaction mixture was stirred at room temperature for four hours and then more 2,4-dichloroisocyante (1 mg) was added. The solution was stirred for 18 hours and then concentrated to dryness. The solid residue was suspended in cold acetonitrile (0.5 mL) and the solid was collected by filtration and washed with acetonitrile (3 mL), water (1 mL) and MeOH (2 mL). The solid was dried under vacuum to afford the desired compound (4 mg, 62%). HPLC tR=4.04 min (YMC S5 Combiscreen ODS 4.6×50 mm, 10-90% aqueous methanol containing 0.2% H$_3$PO$_4$, 4 min gradient, monitored at 220). [M+H]+=469.17.

Example 106

1-(5-{[4-amino-7-(1-methylethyl)pyrrolo[2,1-f][1,2,4]triazin-5-yl]carbonyl}-3-pyridinyl)-3-[4-(4-morpholinyl)-2-{[2-(4-morpholinyl)ethyl]oxy}phenyl]urea

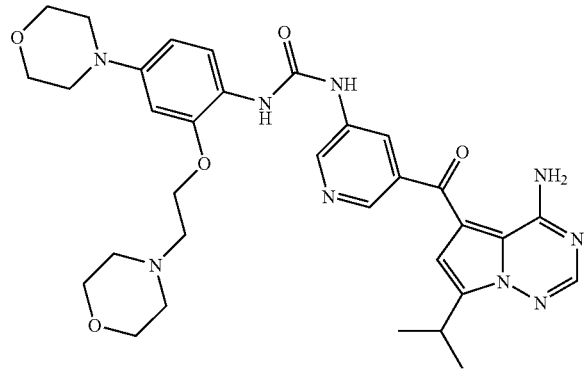

106A. Preparation of 2-(2-bromoethoxy)-4-fluoro-1-nitrobenzene

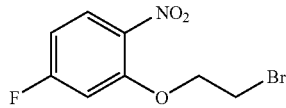

A solution of 5-fluoro-2-nitrophenol (1.5 g, 9.55 mmole) in acetonitrile (100 mL) under a nitrogen atmosphere was treated with potassium carbonate (4.5 g, 32.6 mmole) and 1,2-dibromoethane (16.0 mL, 186 mmole), The reaction mixture was heated to 70° C. for 40 hours. The reaction was then filtered and concentrated. The crude material was purified by flash chromatography (SiO$_2$, 20% ethyl acetate/hexane) to give 2-(2-bromoethoxy)-4-fluoro-1-nitrobenzene (2.5 g, 98%). $^1$HNMR (CDCl$_3$) δ 7.97 (m, 1H), 6.79 (m, 2H), 4.40 (t, 2H, J=8.0 Hz), 3.69 (t, 2H, J =8.0 Hz).

106B. Preparation of 4-(2-(5-morpholino-2-nitrophenoxy)ethyl)morpholine

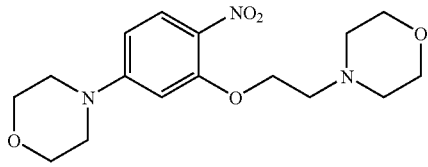

A solution of 2-(2-bromoethoxy)-4-fluoro-1-nitrobenzene (160 mg, 0.6 mmol) in 20 mL acetonitrile under a nitrogen atmosphere was treated with potassium carbonate (360 mg, 2.6 mmol) and morpholine (0.3 mL, 3.4 mmol). The reaction mixture was heated to 70° C. for three hours and then filtered and concentrated. The residue was purified by flash chromatography (SiO$_2$, 100% ethyl acetate/hexane) to give 4-(2-(5-morpholino-2-nitrophenoxy)ethyl)morpholine (50 mg, 25%). $^1$HNMR (CDCl$_3$) δ 7.99 (m, 1H), 6.45 (m, 1H), 6.35 (s, 1H), 4.21 (t, 2H, J=4.0 Hz), 3.85 (t, 4H, J=4.0 Hz), 3.72 (t, 4H, J=4.0 Hz), 3.33 (t, 4H, J=4.0 Hz), 2.89 (t, 2H, J=4.0 Hz), 2.63 (t, 4H, J=4.0 Hz).

106C. Preparation of 4-morpholino-2-(2-morpholinoethoxy)aniline

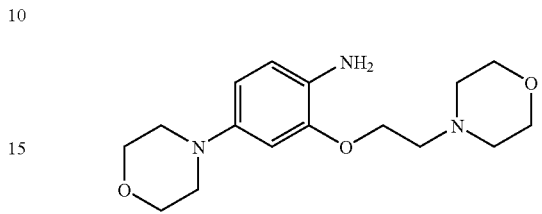

A solution of 106B (50 mg, 0.15mmol) in MeOH (10 mL) was degassed for 10 minutes and then treated with 10% Pd on activated carbon (15 mg). The reaction mixture was stirred at room temperature for 18 hours under a hydrogen atmosphere. The catalyst was removed by filtration and the filtrate was concentrated to give 4-morpholino-2-(2-morpholinoethoxy)aniline (35 mg, 82%).

106D. 1-(5-{[4-amino-7-(1-methylethyl)pyrrolo[2,1-f][1,2,4]triazin-5-yl]carbonyl}-3-pyridinyl)-3-[4-(4-morpholinyl)-2-{[2-(4-morpholinyl)ethyl]oxy}phenyl]urea

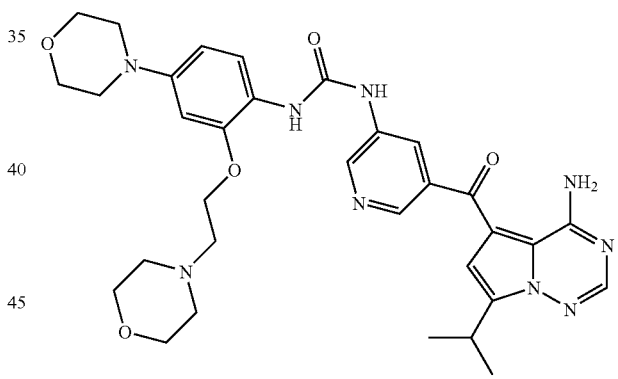

A solution of 4-morpholino-2-(2-morpholinoethoxy)aniline (10 mg, 0.03 mmol) in CH$_2$Cl$_2$ (10 mL) was treated with 1,1'-carbonyldiimidazole (5 mg, 0.08 mmol). The reaction mixture was stirred at room temperature for 5 hours. To this solution was added (4-amino-7-isopropylpyrrolo[1,2-f][1,2,4]triazin-5-yl)(5-aminopyridin-3-yl)methanone (5 mg, 0.016 mmol) and the reaction mixture was stirred at room temperature for three days. The reaction was concentrated and purified by reversed-phase preparative HPLC (YMC ODS-A 20×100 mm, 10-90% aqueous methanol containing 0.1% TFA, 20 min gradient, monitored at 220 nm) to give 1-(5-(4-amino-7-isopropylpyrrolo[1,2-f][1,2,4]triazine-5-carbonyl)pyridin-3-yl)-3-(4-morpholino-2-(2-morpholinoethoxy)phenyl)urea (2 mg, 20%). $^1$HNMR(DMSO-d$_6$) δ 9.46 (s, 1H), 9.17(s, 1H) 8.74 (s, 1H), 8.46 (s, 1H), 8.37 (s, 1H), 8.27 (s, 1H), 8.12 (s, 1H), 8.06 (s, 1H), 7.62 (m, 1H), 6.74 (s, 1H), 6.65 (s, 1H), 6.50 (m, 1H), 4.38 (m, 2H), 3.90 (m, 2H), 3.69 (m, 4H), 3.63 (m, 2H), 3.54 (m, 4H), 3.34 (m, 1H), 3.17

(m, 2H), 3.04 (m, 4H), 1.22 (d, 6H, J=5.0 Hz). HPLC $R_f$=2.58 min. (Chromolith SpeedROD 4.6×50 mm, 10-90% aqueous methanol containing 0.1% TFA, 4 min gradient, monitored at 220 or 254 nm). m/z=630.43 (M+H$^+$).

Example 107

1-(3-{[4-amino-7-(1-methylethyl)pyrrolo[2,1-f][1,2,4]triazin-5-yl]carbonyl}phenyl)-3-(4-{[3-(4-morpholinyl)propyl]oxy}phenyl)urea

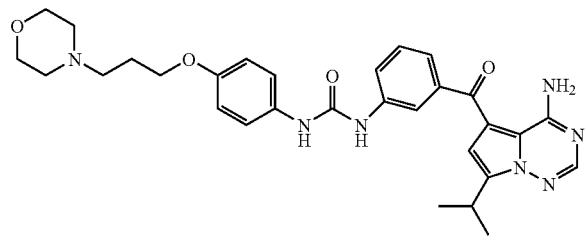

107A. Preparation of Methyl 4-(3-bromopropoxy)benzoate

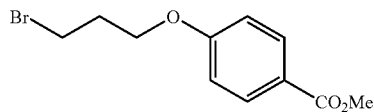

A mixture of methyl 4-hydroxybenzoate (1.52 g, 10 mmol), 1,3-dibromo-propane (20.3 mL, 200 mmol) and potassium carbonate (4.2 g, 30 mmol) in 100 mL of dry CH$_3$CN was heated at 70° C. for 5.0 hr. After cooling to room temperature, the reaction mixture was filtered through a pad of Celite and rinsed with CH$_3$CN. The combined filtrates were concentrated in vacuo and purified by ISCO (Hexane-ethyl acetate: 80:20 to 0:100) on silica gel to afford 107A (2.44 g, 89%) as an oil.

107B. Preparation of 4-(3-bromopropoxy)benzoic acid

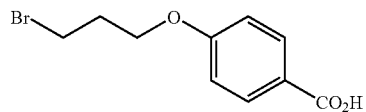

A mixture of 107A (2.44 g, 8.9 mmol) and lithium hydroxide monohydrate (750 mg, 17.9 mmol) in THF-H2O-MeOH (15:7:7, 29 mL) was stirred at 60° C. for 2.0 hr. After cooling to room temperature, the reaction mixture was diluted with water (30 mL) and concentrated in vacuo to remove most organic solvents. The mixture was washed with 1:1 mixture of ethyl acetate-ether and the aqueous layer was acidified with 2.0 N HCl to pH 5.0. The precipitate was collected by filtration, rinsed with water and dried under high vacuum to give 107B as a crystalline solid (1.64 g, 71%).

107C. Preparation of 1-(3-(4-amino-7-isopropylpyrrolo[1,2-f][1,2,4]triazine-5-carbonyl)phenyl)-3-(4-(3-bromopropoxy)phenyl)urea

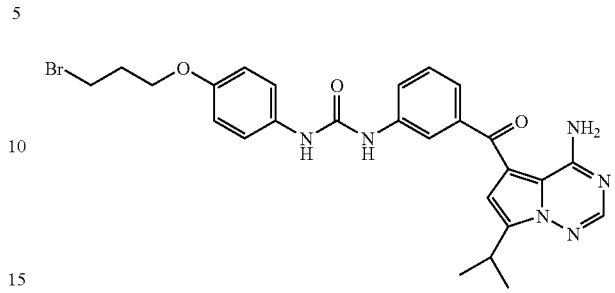

To a solution of 107B (31 mg, 0.12 mmol) in dry 1,4-dioxane (0.5 mL) was added triethyl amine (0.02 mL, 0.144 mmol), followed by diphenylphosphoryl azide (0.03 mL, 0.144 mmol). After heating at 80° C. for 2.0 hr, the reaction was cooled to room temperature, concentrated in vacuo and directly used in the next step reaction without further purification.

Compound 1H (30 mg, 0.1 mmol) was dissolved in MeOH (1 ml) containing TFA (2 drops) and stirred briefly for 5 min, concentrated and dried under high vacuum for 30 min. The residue was dissolved in dry CH$_3$CN (2 ml), crude isocyanate prepared above (ca. 0.12 mmol) in 1.0 mL of dry CH$_3$CN was added in one portion. The reaction mixture was stirred at RT overnight and concentrated to dryness. Purification with reverse-phase preparative HPLC gave 34.5 mg of 107C as a solid.

107D. Preparation of 1-(3-(4-amino-7-isopropylpyrrolo[1,2-f][1,2,4]triazine-5-carbonyl)phenyl)-3-(4-(3-morpholinopropoxy)phenyl)urea

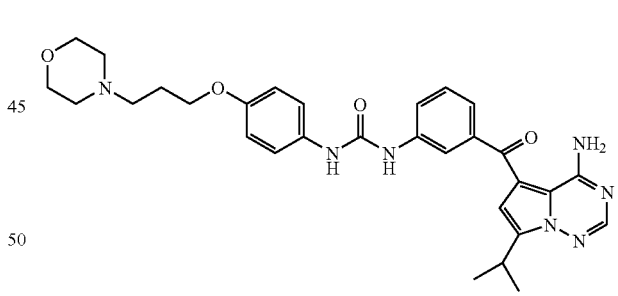

A mixture of 107C (34.3 mg, 0.062 mmol), morpholine (0.0081 mL, 0.093 mmol) and diisopropylethyl amine (0.022 mL, 0.124 mmol) in 1.0 mL of dry DMF was heated at 80° C. for 2.0 hr. After cooled to room temperature, the reaction was directly purified by reverse-phase preparative HPLC to afford 18 mg of 107D as a white solid. $^1$HNMR (DMSO-d$_6$) δ 9.28 (bs, 1H), 8.84 (s, 1H), 8.55 (s, 1H), 8.33 (s, 1H), 8.12 (s, 1H), 7.93 (s, 1H), 7.60 (m, 1H), 7.44 (m, 1H), 7.33 (m, 2H), 6.85 (m, 2H), 6.78 (s, 1H), 3.94 (m, 2H), 3.56 (m, 4H), 3.32 (m, 4H), 2.35 (m, 3H), 1.83 (m, 1H), 1.27 (m, 6H), 1.24 (m, 2H). HPLC $R_f$=2.716 min. (Chromolith SpeedROD 4.6×50 mm, 10-90% aqueous methanol containing 0.1% TFA, 4 min gradient, monitored at 254 nm). m/z=558.22 (M+H$^+$).

Example 108

N-(3-{[4-amino-7-(1-methylethyl)pyrrolo [2,1-f][1,2,4]triazin-5-yl]carbonyl}phenyl)-2,3-dihydro-4H-1,4-benzoxazine-4-carboxamide

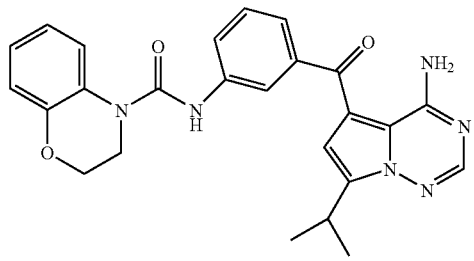

108A. Preparation of 1-(3-(4-amino-7-isopropylpyrrolo[1,2-f][1,2,4]triazine-5-carbonyl)phenyl)-3-(2-hydroxyphenyl)urea

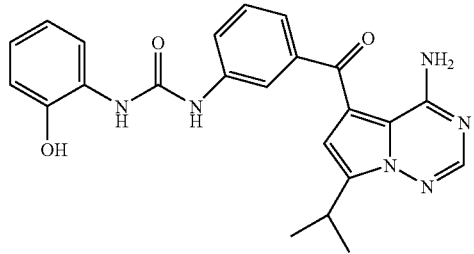

A solution of 14 (130 mg, 0.29 mmol) in CH$_2$Cl$_2$ (3 mL) at −78° C. was treated with BBr$_3$ (1.0 M in CH$_2$Cl$_2$, 0.59 mL, 0.59 mmol) dropwise. The reaction mixture was allowed to warm to ambient temperature for 30 minutes. The reaction mixture was then concentrated under reduced pressure and diluted with THF. Water was added to the solution and the solvents were removed under reduced pressure. The crude product was purified by flash chromatography (SiO$_2$, 5% MeOH/CH$_3$Cl) to afford the desired product (91 mg, 72%).

108B. Preparation of 2-chloroethyl trifluoromethanesulfonate

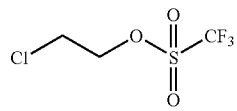

A solution of triflic anhydride (2.0 mL, 11.9 mmol) in CCl$_4$ (10 mL) at 0° C. was treated with a solution of 2-chloroethanol (0.8 mL, 11.9 mmol) and pyridine (0.96 mL, 11.9 mmol) in CCl$_4$ (6.0 mL) which was pre-cooled to 0° C. The reaction mixture was stirred at 0° C. for 45 minutes and then filtered through a pad of Na$_2$SO$_4$. The filtrate was concentrated and used immediately in the next step.

108C. Preparation of 1-(3-(4-amino-7-isopropylpyrrolo[1,2-f][1,2,4]triazine-5-carbonyl)phenyl)-3-(2-(2-chloroethoxy)phenyl)urea

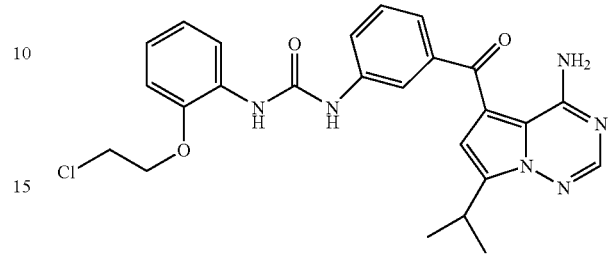

A solution if 108A (91 mg, 0.21 mmol) in 1,2-dichloroethane (1 mL) was treated with a solution of 108B (59 mg, 0.28 mmol) in 1,2-dichloroethane (2.0 mL). 1,2,2,6,6-Pentamethylpiperidine (0.11 mL, 0.63 mmol) was added and the reaction mixture was heated to 65° C. for 30 minutes and then 65° C. for 90 minutes. The reaction mixture was cooled to ambient temperature and purified by flash chromatography (SiO$_2$, 5% MeOH/CH$_3$Cl) to afford the desired compound (70 mg, 67%). HPLC $t_R$=3.75 min (Waters Sunfire C18 4.6×50 mm column 10-90% aqueous methanol containing 0.1% TFA, 4 min grad. monitored at 220 nm).

108D. Preparation of 1-(3-{[4-amino-7-(1-methylethyl)pyrrolo [2,1-f][1,2,4]triazin-5-yl]carbonyl}phenyl)-3-(2-{[2-(4-morpholinyl)ethyl]oxy}phenyl)urea

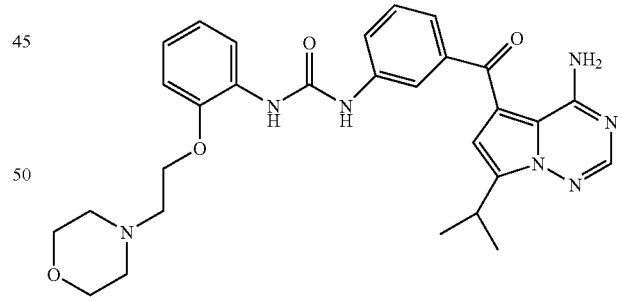

A solution of 108C (16 mg, 0.03 mmol) in morpholine (1.0 mL) was stirred at room temperature for two hours. The temperature was then raised to 50° C. for 3 hours and the reaction was then concentrated to dryness. The crude product was purified by preparative reversed phase HPLC to afford the desired compound (10 mg). HPLC $t_R$=1.67 min (Phenomenex Luna 5u C18 4.6×30 mm column 10-90% aqueous methanol containing 0.1% TFA, 2 min grad. monitored at 220 nm). [M+H]$^+$=544.31.

Example 109

N-(3-{[4-amino-7-(1-methylethyl)pyrrolo[2,1-f][1,2,4]triazin-5-yl]carbonyl}phenyl)-2,3-dihydro-4H-1,4-benzoxazine-4-carboxamide

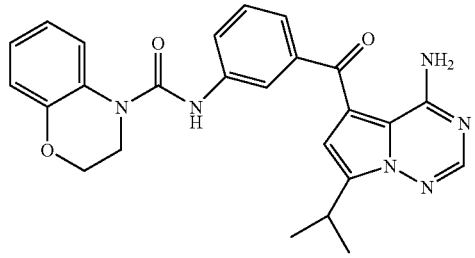

A solution of 108C (23 mg, 0.05 mmol) in DMF (1.0 mL) was treated with K$_2$CO$_3$ (77 mg, 0.56 mmol) and morpholine (0.04 mL, 0.47 mmol) at room temperature. The reaction was stirred for 20 hours and then concentrated to dryness. The crude product was purified by flash chromatography (SiO$_2$, 3% MeOH/CH$_3$Cl) to afford the desired compound (12 mg). HPLC t$_R$=1.92 min (Phenomenex Luna 5u C18 4.6×30 mm column 10-90% aqueous methanol containing 0.1% TFA, 2 min grad. monitored at 220 nm). [M+H]$^+$=457.25.

Example 110

1-(3-{[4-amino-7-(1-methylethyl)pyrrolo[2,1-f][1,2,4]triazin-5-yl]carbonyl}phenyl)-3-(2-{[2-(1-piperazinyl)ethyl]oxy}phenyl)urea

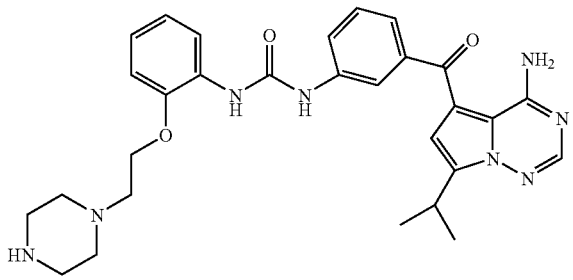

A solution of 108C (5 mg, 0.01 mmol) in N,N-dimethylformamide (0.5 mL) saturated with piperazine was stirred at room temperature for one hour. The temperature was then raised to 60° C. for two hours and the reaction was then concentrated to dryness. The crude product was purified by preparative reversed phase HPLC to afford the desired compound (3 mg). HPLC t$_R$=1.65 min (Phenomenex Luna 5u C18 4.6×30 mm column 10-90% aqueous methanol containing 0.1% TFA, 2 min grad. monitored at 220 nm). [M+H]$^+$=543.29.

We claim:

1. A compound of formula II

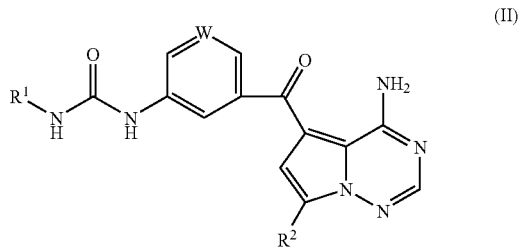

wherein

W is —CR$^9$— or —N—;

R$^1$ is H, C$_1$-C$_6$ alkyl, arylalkyl, C$_3$-C$_8$ cycloalkyl, C$_9$-C$_{14}$ bicycloalkyl, C$_6$-C$_{10}$ aryl, C$_5$-C$_{13}$ heteroaryl, C$_4$-C$_{12}$ heterocyclyl and 3 to 8- membered heterocycloalkyl and each of said groups optionally substituted with 1 to 3 groups selected from the group consisting of halogen, —OH, —OR$^7$, —C(=O)OR$^7$—, —S(=O)NHR$^7$, —SO$_2$NHR$^7$, —SO$_2$R$^7$, alkyl, substituted alkyl, —CN, —NHR$^7$, —CONHR$^7$, —OCONHR$^7$, —CONHSO$_2$R$^7$, —NHCONHR$^7$, —CH$_2$OR$^7$, —CH$_2$CH$_2$OH, alkoxy, substituted alkoxy, aryl or substituted aryl, R$^7$ is hydrogen or C$_1$-C$_4$ alkyl; C$_3$-C$_6$ cycloalkyl, aryl, arylalkyl, heteroaryl, heterocyclyl, aryloxy, substituted aryloxy, —CF$_3$ and —OCF$_3$, two of which may be attached to the same ring carbon atom;

R$^2$ is hydrogen, halogen, —NR$^8$R$^9$, C$_1$-C$_6$ alkyl, C$_1$-C$_6$ alkenyl, C$_1$-C$_6$ alkynyl, C$_3$-C$_8$ cycloalkyl, arylalkyl or C$_4$-C$_8$ heterocyclyl with at least one atom on the ring selected from nitrogen or oxygen atom, and each of said R$^2$ groups optionally substituted with 1 to 3 groups selected from the group consisting of —OH, OR$^8$, —NH$_2$, —NR$^8$R$^9$, —CONHR$^8$, —OCONHR$^8$, —CONHSO$_2$R$^8$, —NHCONHR$^8$, —SR$^8$, —S(=O)R$^8$, —SO$_2$R$^8$, —SO$_2$N R$^8$R$^9$;

R$^8$ is C$_1$-C$_6$ alkyl, C$_3$-C$_6$ cycloalkyl, an optionally substituted aryl or heteroaryl group; said substituents on the substituted aryl or substituted heteroaryl group are selected from the group consisting of one or more hydrogen, halogen, alkyl, substituted alkyl, alkynyl, substituted alkynyl, alkoxy, substituted alkoxy, aryl, substituted aryl, arylalkyl, substituted arylalkyl, aryloxy and substituted aryloxy;

R$^9$ is hydrogen, halogen, C$_1$-C$_6$ alkyl, C$_3$-C$_6$ cycloalkyl or C$_1$-C$_6$ alkoxy; or R$^8$ and R$^9$ can be taken together with the nitrogen atom to which they are attached to form an optionally substituted heterocyclyl ring;

or a pharmaceutically acceptable salt or stereoisomer thereof.

2. A compound of the formula III (III)

wherein
W is —CR$^9$— or —N—;
R$^1$ is H, C$_1$-C$_6$ alkyl, arylalkyl, C$_3$-C$_8$ cycloalkyl, C$_9$-C$_{14}$ bicycloalkyl, C$_6$-C$_{10}$ aryl, C$_5$-C$_{13}$ heteroaryl, C$_4$-C$_{12}$ heterocyclyl and 3 to 8-membered heterocycloalkyl and each of said groups optionally substituted with 1 to 3 groups selected from the group consisting of halogen, —OH, —OR$^7$, —C(=O)OR$^7$—, —S(=O)NHR$^7$, —SO$_2$NHR$^7$, —SO$_2$R$^7$, alkyl, substituted alkyl, —CN, —NHR$^7$, —CONHR$^7$, —OCONHR$^7$, —CONHSO$_2$R$^7$, —NHCONHR$^7$, —CH$_2$OR$^7$, —CH$_2$CH$_2$OH, alkoxy, substituted alkoxy, aryl or substituted aryl,
R$^7$ is hydrogen or C$_1$-C$_4$ alkyl; C$_3$-C$_6$ cycloalkyl, aryl, arylalkyl, heteroaryl, heterocyclyl, aryloxy, substituted aryloxy, —CF$_3$ and —OCF$_3$, two of which may be attached to the same ring carbon atom;
or a pharmaceutically acceptable salt or stereoisomer thereof.

3. A compound selected from the group consisting of
1-(5-{[4-amino-7-(1-methylethyl)pyrrolo[2,1-f][1,2,4]triazin-5-yl]carbonyl}-3-pyridinyl)-3-(2,4-dichlorophenyl)urea;
1-(3-{[4-amino-7-(1-methylethyl)pyrrolo[2,1-f][1,2,4]triazin-5-yl]carbonyl}phenyl)-3-[3-(1,1-dimethylethyl)-1-methyl-1H-pyrazol-5-yl]urea;
1-(5-{[4-amino-7-(1-methylethyl)pyrrolo[2,1-f][1,2,4]triazin-5-yl]carbonyl}-3-pyridinyl)-3-(2,4-difluorophenyl)urea;
1-(5-{[4-amino-7-(1-methylethyl)pyrrolo[2,1-f][1,2,4]triazin-5-yl]carbonyl}-3-pyridinyl)-3-(2-fluorophenyl)urea;
1-(3-{[4-amino-7-(1-methylethyl)pyrrolo[2,1-f][1,2,4]triazin-5-yl]carbonyl}phenyl)-3-(3-cyclopropyl-1-methyl-1H-pyrazol-5-yl)urea;
1-(5-{[4-amino-7-(1-methylethyl)pyrrolo[2,1-f][1,2,4]triazin-5-yl]carbonyl}-3-pyridinyl)-3-(4-chlorophenyl)urea;
1-(5-{[4-amino-7-(1-methylethyl)pyrrolo[2,1-f][1,2,4]triazin-5-yl]carbonyl}-3-pyridinyl)-3-(2-cyanophenyl)urea;
1-(5-{[4-amino-7-(1-methylethyl)pyrrolo[2,1-f][1,2,4]triazin-5-yl]carbonyl}-3-pyridinyl)-3-[1-methyl-3-(1-methylethyl)-1H-pyrazol-5-yl]urea;
1-[5-({4-amino-7-[3-(dimethylamino)-1-propyn-1-yl]pyrrolo[2,1-f][1,2,4]triazin-5-yl}carbonyl)-3-pyridinyl]-3-(2,4-dichlorophenyl)urea;
1-(5-{[4-amino-7-(1-methylethyl)pyrrolo[2,1-f][1,2,4]triazin-5-yl]carbonyl}-3-pyridinyl)-3-[2-(trifluoromethyl)phenyl]urea;
1-(3-(4-amino-7-(3-(dimethylamino)prop-1-ynyl)pyrrolo[1,2-f][1,2,4]triazine-5-carbonyl)phenyl)-3-(2,4-dichlorophenyl)urea;
1-{3-[(4-amino-7-isopropyl-pyrrolo[2,1-f][1,2,4]triazin-5-yl)carbonyl]phenyl}-3-[4-(trifluoromethyl)phenyl]urea;
1-(3-{[4-amino-7-(1-methylethyl)pyrrolo[2,1-f][1,2,4]triazin-5-yl]carbonyl}phenyl)-3-[3-(1,1-dimethylethyl)-1-(2-hydroxyethyl)-1H-pyrazol-5-yl]urea;
1-{3-[(4-amino-7-isopropyl-pyrrolo[2,1-f][1,2,4]triazin-5-yl)carbonyl]phenyl}-3-(4-bromophenyl)urea;
1-{3-[(4-amino-7-bromopyrrolo[2,1-f][1,2,4]triazin-5-yl)carbonyl]phenyl}-3-(3-cyclopropyl-1-methyl-1H-pyrazol-5-yl)urea;
1-{3-[(4-amino-7-bromopyrrolo[2,1-f][1,2,4]triazin-5-yl)carbonyl]phenyl}-3-(2,4-dichlorophenyl)urea;
1-(3-{[4-amino-7-(1-methylethyl)pyrrolo[2,1-f][1,2,4]triazin-5-yl]carbonyl}phenyl)-3-{3-cyclopropyl-1-[2-(4-morpholinyl)ethyl]-1H-pyrazol-5-yl}urea;
1-(5-{[4-amino-7-(1-methylethyl)pyrrolo[2,1-f][1,2,4]triazin-5-yl]carbonyl}-3-pyridinyl)-3-[4-(dimethylamino)phenyl]urea;
1-[3-({4-amino-7-[3-(dimethylamino)-1-propyn-1-yl]pyrrolo[2,1-f][1,2,4]triazin-5-yl}carbonyl)phenyl]-3-(3-cyclopropyl-1-methyl-1H-pyrazol-5-yl)urea;
1-{3-[(4-amino-7-isopropylpyrrolo[2,1-f][1,2,4]triazin-5-yl)carbonyl]phenyl}-3-(2,4-dichlorophenyl)urea;
1-{3-[(4-amino-7-isopropyl-pyrrolo[2,1-f][1,2,4]triazin-5-yl)carbonyl]phenyl}-3-phenylurea;
1-{3-[(4-amino-7-isopropyl-pyrrolo[2,1-f][1,2,4]triazin-5-yl)carbonyl]phenyl}-3-(2-methoxyphenyl)urea;
1-{3-[(4-amino-7-isopropyl-pyrrolo[2,1-f][1,2,4]triazin-5-yl)carbonyl]phenyl}-3-[2-(trifluoromethyl)phenyl]urea;
1-{3-[(4-amino-7-isopropyl-pyrrolo[2,1-f][1,2,4]triazin-5-yl)carbonyl]phenyl}-3-(3-methoxyphenyl)urea;
1-{3-[(4-amino-7-isopropyl-pyrrolo[2,1-f][1,2,4]triazin-5-yl)carbonyl]phenyl}-3-(3-methylphenyl)urea;
1-{3-[(4-amino-7-isopropyl-pyrrolo[2,1-f][1,2,4]triazin-5-yl)carbonyl]phenyl}-3-(4-fluorophenyl)urea;
1-{3-[(4-amino-7-isopropyl-pyrrolo[2,1-f][1,2,4]triazin-5-yl)carbonyl]phenyl}-3-(4-phenoxyphenyl)urea;
1-{3-[(4-amino-7-isopropyl-pyrrolo[2,1-f][1,2,4]triazin-5-yl)carbonyl]phenyl}-3-(2,4-dimethylphenyl)urea;
1-{3-[(4-amino-7-isopropyl-pyrrolo[2,1-f][1,2,4]triazin-5-yl)carbonyl]phenyl}-3-(1-naphthyl)urea;
1-{3-[(4-amino-7-isopropyl-pyrrolo[2,1-f][1,2,4]triazin-5-yl)carbonyl]phenyl}-3-[4-(dimethylamino)phenyl]urea;
1-{3-[(4-amino-7-isopropyl-pyrrolo[2,1-f][1,2,4]triazin-5-yl)carbonyl]phenyl}-3-[4-(benzyloxy)phenyl]urea;
1-{3-[(4-amino-7-isopropyl-pyrrolo[2,1-f][1,2,4]triazin-5-yl)carbonyl]phenyl}-3-pyridin-3-ylurea;
1-{3-[(4-amino-7-isopropyl-pyrrolo[2,1-f][1,2,4]triazin-5-yl)carbonyl]phenyl}-3-(1,3-benzodioxol-5-yl)urea;
1-{3-[(4-amino-7-isopropyl-pyrrolo[2,1-f][1,2,4]triazin-5-yl)carbonyl]phenyl}-3-(2-naphthyl)urea;
1-{3-[(4-amino-7-isopropyl-pyrrolo[2,1-f][1,2,4]triazin-5-yl)carbonyl]phenyl}-3-biphenyl-2-ylurea;
or a pharmaceutically acceptable salt thereof.

4. A pharmaceutical composition comprising one or more compounds of claim 1 and a pharmaceutically acceptable carrier.

5. A pharmaceutical composition comprising one or more compounds of claim 2 and a pharmaceutically acceptable carrier.

6. A pharmaceutical composition comprising one or more compounds of claim 3 and a pharmaceutically acceptable carrier.

* * * * *